United States Patent [19]

Hagiwara et al.

[11] Patent Number: 5,363,187
[45] Date of Patent: Nov. 8, 1994

[54] LIGHT SCANNING APPARATUS FOR DETECTING FOREIGN PARTICLES ON SURFACE HAVING CIRCUIT PATTERN

[75] Inventors: Tsuneyuki Hagiwara, Tokyo; Fuminori Hayano, Yokohama, both of Japan

[73] Assignee: Nikon Corporation, Tokyo, Japan

[21] Appl. No.: 76,697

[22] Filed: Jun. 15, 1993

Related U.S. Application Data

[63] Continuation of Ser. No. 995,527, Dec. 22, 1992, abandoned, which is a continuation of Ser. No. 757,042, Sep. 9, 1991, abandoned.

[30] Foreign Application Priority Data

Sep. 12, 1990 [JP] Japan ................. 2-242247

[51] Int. Cl.$^5$ ........................... G01N 21/88
[52] U.S. Cl. .................. 356/237; 250/563; 250/572
[58] Field of Search .............. 356/237; 250/572, 563

[56] References Cited

U.S. PATENT DOCUMENTS

| | | | |
|---|---|---|---|
| 4,468,120 | 8/1984 | Tanimoto et al. | 356/237 |
| 4,889,998 | 12/1989 | Hayano et al. | 250/563 |
| 4,943,734 | 7/1990 | Johnson et al. | 250/572 |
| 4,952,058 | 8/1990 | Noguchi et al. | 356/237 |

FOREIGN PATENT DOCUMENTS 61-230048 10/1986 Japan .
1-239437 9/1989 Japan .

OTHER PUBLICATIONS

Patent Abstracts of Japan, vol. 13, No. 572 (P-978) (3920) 18 Dec. 1989.
Patent Abstracts of Japan, vol. 14, No. 11 (P-988) (3954) 11 Jan. 1990.
Patent Abstracts of Japan, vol. 11, No. 66 (P-552) (2513) 27 Feb. 1987.
Patent Abstracts of Japan, vol. 9, No. 321 (E-367) 17 Dec. 1985.

*Primary Examiner*—Vincent P. McGraw
*Attorney, Agent, or Firm*—Shapiro and Shapiro

[57] ABSTRACT

A foreign particle detecting apparatus comprises a light source for radiating coherent light onto an object to be detected on a surface of which a circuit pattern is formed, a focusing device for focusing the light emitted from the light source onto the object to be detected at a predetermined angular aperture, a device for moving the incident light focused at the predetermined angular aperture relative to the object to be detected, and a detector for receiving scattered light produced upon incidence of the focused light onto the object to be detected, and which detects foreign matter on the object to be detected on the basis of an output signal from the detector. Foreign matter is discriminated from the circuit pattern on the basis of the output signal from the detector means. The detector comprises at least two light-receiving elements, separated by a spatial angle substantially equal to or slightly larger than the angular aperture of the incident light, for individually outputting signals.

26 Claims, 17 Drawing Sheets

STRENGTH

PATTERN ①

PATTERN ②

PATTERN ③

FOREIGN MATTER

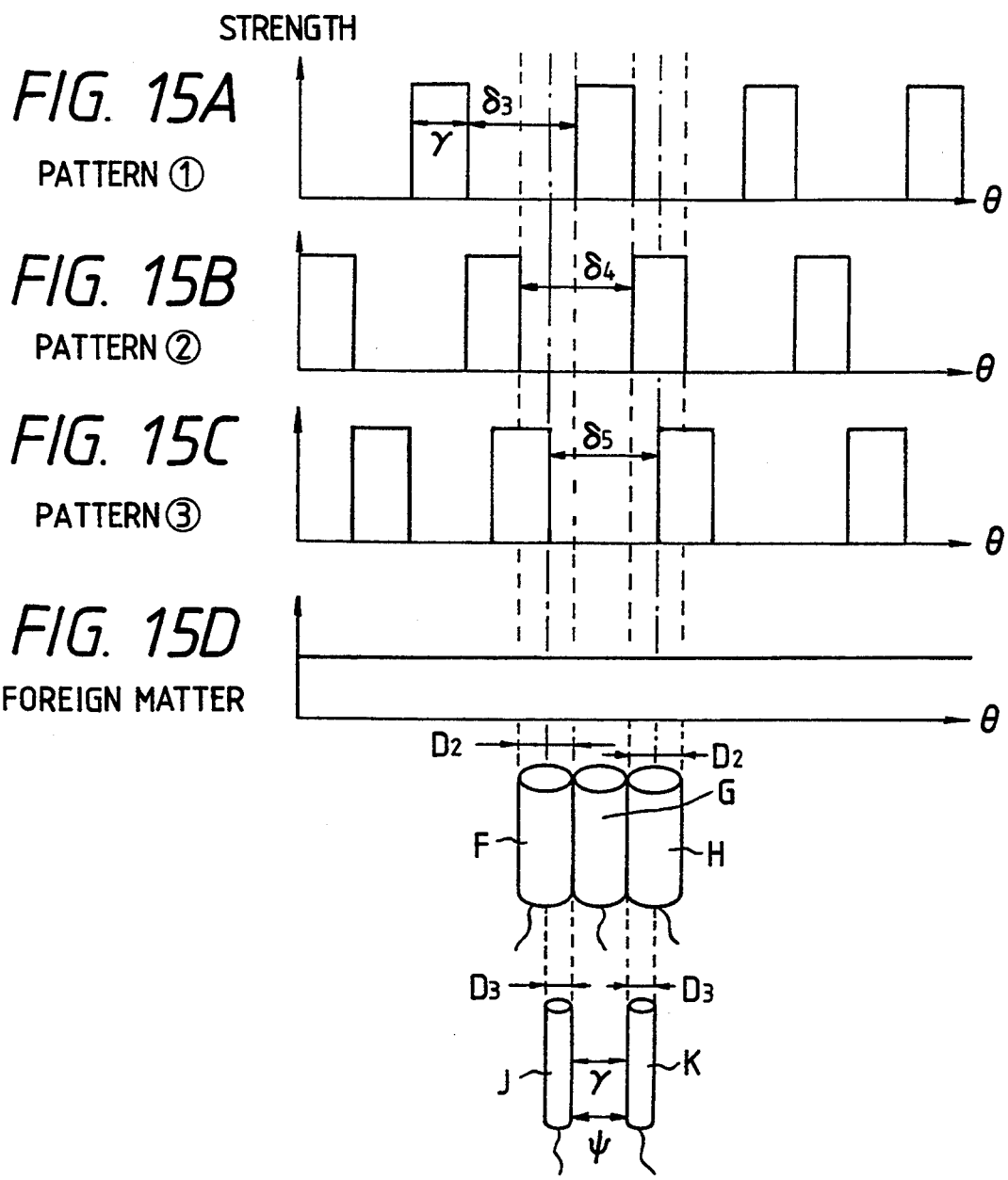
FIG. 15A PATTERN ①
FIG. 15B PATTERN ②
FIG. 15C PATTERN ③
FIG. 15D FOREIGN MATTER

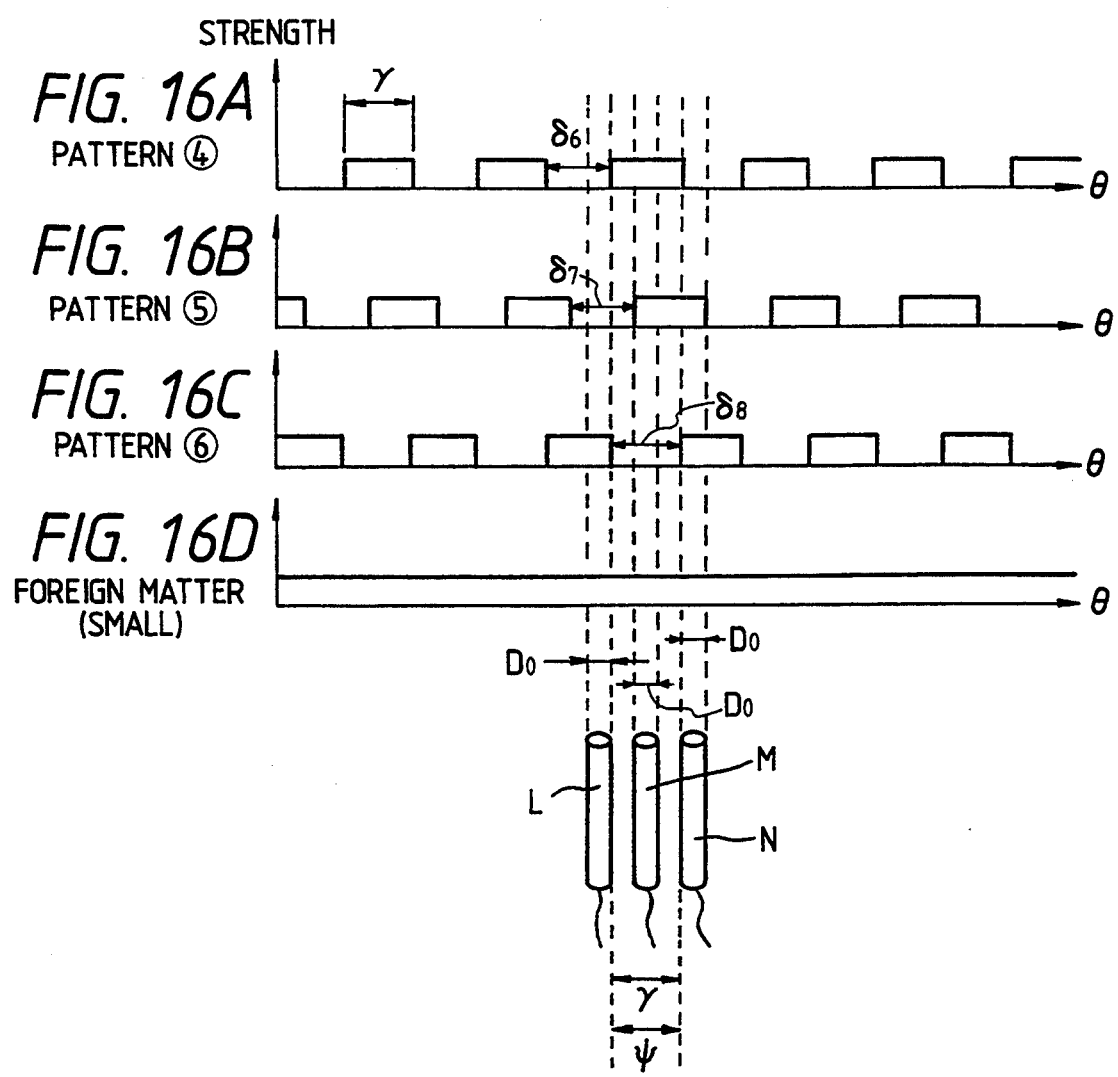

LIGHT SCANNING APPARATUS FOR DETECTING FOREIGN PARTICLES ON SURFACE HAVING CIRCUIT PATTERN

This is a continuation of application Ser. No. 995,527 filed Dec. 22, 1992, which is a continuation of application Ser. No. 757,042 filed Sep. 9, 1991, both now abandoned.

BACKGROUND OF THE INVENTION

1. Field of the Invention

The present invention relates to a foreign particle detecting apparatus and, more particularly, to a foreign particle detecting apparatus for detecting foreign particles or foreign matter (e.g., non-transparent dust) attached to a substrate such as a reticle, a photomask, a semiconductor wafer, or the like used in a semiconductor manufacturing apparatus.

2. Related Background Art

In an IC manufacturing process, an exposure circuit pattern formed on a substrate such as a reticle, a photomask, or the like is transferred onto a wafer surface coated with a resist using a semiconductor printing apparatus (stepper or aligner). In this case, if foreign matter such as dust is present on the substrate surface, the foreign matter is transferred onto the wafer surface together with the circuit pattern, thus decreasing the yield in the manufacture of ICs. For this reason, it is indispensable to detect foreign matter on the substrate in the IC manufacturing process. As described in U.S. Pat. No. 4,468,120, and the like, various detecting methods have been proposed.

FIG. 17 shows a conventional foreign particle detecting apparatus. Coherent light emitted from a laser light source 11 is converted into a parallel light beam having an increased spot size by a beam expander 12. The parallel light beam with the increased spot size is obliquely projected on the surface of a substrate 15 via a scanning mirror 13 and a scanning lens or an f-$\theta$ lens 14. In this case, the scanning mirror 13 is rotated or vibrated to one-dimensionally scan the beam on the substrate 15 in the x direction. At the same time, a stage (not shown) for mounting the substrate 15 is moved in the y direction. Thus, foreign matter attached onto the substrate surface can be detected over substantially the entire region of the surface of the substrate 15. A plurality of light-receiving elements 166, 167, and 168 are arranged at positions separated from optical paths of regular reflected light and regular transmission light from the substrate. The presence/absence of foreign matter on the substrate 15 is detected using output signals from the plurality of light-receiving elements 166, 167, and 168.

In this apparatus, since the spatial distribution of scattered light from the circuit pattern has strong directivity, output values from the light-receiving elements are extremely different from each other. In contrast to this, since the spatial distribution of scattered light from foreign matter has no directivity, the output signals from the light-receiving elements become almost equal to each other. Therefore, the output values from the light-receiving elements are compared with each other to discriminate foreign matter from the circuit pattern.

However, in recent years, miniaturization of IC circuit patterns leads to miniaturization of circuit patterns on substrates such as reticles or photomasks. As a result, the spatial distribution of scattered light from a circuit pattern becomes isotropic, and tends to have no directivity. In other words, the output values from the light-receiving elements for receiving diffracted light from the circuit pattern tend to be equal to each other.

Therefore, almost no difference among output values from the light-receiving elements is observed between foreign matter and the circuit pattern, and it becomes difficult to discriminate foreign matter from the circuit pattern. In addition, miniaturization of circuit patterns requires an increase in detection resolution.

SUMMARY OF THE INVENTION

It is an object of the present invention to provide a foreign particle detecting apparatus which can detect foreign matter and a circuit pattern at a high selective detection rate.

One aspect of the present invention has been established in consideration of the following fact.

When foreign matter attached onto a substrate having a miniaturized circuit pattern which produces relatively nondirectional scattered light is to be detected:

① When the circuit pattern has periodicity, diffracted light from the circuit pattern is discretely distributed, and the distribution interval is increased as the degree of miniaturization of the circuit pattern is increased.

② The angular aperture of diffracted light discretely produced from the circuit pattern becomes almost equal to that of incident light independently of the circuit pattern.

Another aspect of the present invention has been established in consideration of the fact that the circuit pattern of a memory IC such as a DRAM manufactured by patterning with a relatively high degree of miniaturization includes many two-dimensional periodic patterns, and most of the two-dimensional periodic patterns have periodicity in the X and Y directions of a substrate (to be simply referred to as "X and Y directions" hereinafter), or are line-symmetrical about the X or Y direction.

A foreign particle detecting apparatus according to the present invention, which comprises a light source for radiating coherent light onto an object to be detected on a surface of which a circuit pattern is formed, focusing means for focusing the light emitted from the light source onto the object to be detected at a predetermined angular aperture, moving means for moving the incident light focused at the predetermined angular aperture relative to the object to be detected, and detecting means for receiving scattered light produced upon incidence of the focused light onto the object to be detected, and which detects foreign matter on the object to be detected on the basis of an output signal from the detecting means, comprises discrimination means for discriminating foreign matter from the circuit pattern on the basis of the output signal from the detecting means. The detecting means comprises at least two light-receiving elements, separated by a spatial angle substantially equal to or slightly larger than the angular aperture of the incident light, for individually outputting signals.

The principle of discriminating foreign matter from a circuit pattern according to the present invention will be described below with reference to the accompanying drawings. Prior to the description of the principle, a distribution state of diffracted light obtained when incident light having a predetermined angular aperture is incident on a circuit pattern will be explained.

FIG. 8A is an explanatory view of incident light I incident onto a substrate 15 and diffracted light produced from a circuit pattern A1 on the substrate 15. Scattered light having regularity in a spatial strength distribution is produced from the pattern. Of the scattered light, diffracted light which forms a particularly strong spatial strength distribution will be described below. The circuit pattern A1 is assumed to be a diffraction-grating-like repetitive pattern defined by aligning a plurality of rectangular marks (bar marks) at a predetermined pitch in the Y direction. A plane which includes a line n perpendicular to the substrate 15, and is perpendicular to a reference coordinate axis X on the substrate 15 is assumed to be a plane of incidence, and coherent light I which becomes incident on a point O on the substrate 15 at an incident angle $\alpha$ and an angular aperture $\gamma$ on the plane of incidence is assumed.

For the sake of simplicity, a sphere S illustrated to have a central point O will be examined. In this case, the circuit pattern surface of the substrate 15 is assumed to coincide with the equatorial plane (plane including the diameter of the sphere S) of the sphere S, and a point where the principal ray of the light I crosses the sphere S is represented by Ri.

The angular aperture of regularly reflected light I2 on the plane of incidence is substantially equal to the angular aperture $\gamma$ of the incident light I, and a point Re is a point where the principal ray of the regularly reflected light I2 crosses the sphere S.

When the incident light I becomes incident on the circuit pattern A1, spatially discrete diffracted light components De1, De2, and De3 are produced from the circuit pattern A1. Note that the diffracted light component De3 is 0th-order diffracted light. In this case, the spatial distribution of the diffracted light components De1 to De3 is simple, that is, the diffracted light components De1 to De3 are distributed on a line of intersection Se between the sphere S and the plane of incidence. In other words, the diffracted light components De1 to De3 are spatially discretely distributed on the line of intersection Se between the sphere S and a half-circle having the center O (the incident point of the light I onto the substrate 15) of the sphere S as the center, as indicated by a dotted curve. The line of intersection Se includes the points Ri and Re in the curve.

FIG. 8B is a normal projection view of the spatial distribution of the diffracted light components De1 to De3 on the sphere S when viewed from the direction of the line n onto the equatorial plane. As shown in FIG. 8B, the diffracted light components De1 to De3 are distributed on the line of intersection Se (in this case, the line Se overlaps the reference axis Y of the substrate 15 when viewed from the direction of the line n). In FIG. 8A, points Ed and St represent intersections between the line of intersection Se and the substrate 15, and an angle $\theta_0$ represents an exit angle of regularly reflected light (0th-order diffracted light). The exit angle means a spatial angle from the substrate 15 to have the point O as the center in a direction from the intersection St toward the intersection Ed on the line of intersection (on the line of intersection between a plane where diffracted light components are distributed, and the sphere S).

A case will be examined below wherein the light I is incident on a circuit pattern A2 on the substrate 15 like in FIG. 8A. FIG. 9A shows this case. The circuit pattern A2 is a diffraction-grating-like repetitive pattern defined by aligning a plurality of rectangular marks (bar marks) at a predetermined pitch in the Y' direction inclined from the reference axis Y by an angle $\beta$. Diffracted light components De1', De2', De3', and De4' from the circuit pattern A2 are spatially distributed on a line of intersection Se'. Note that the light component De4' corresponds to 0th-order diffracted light component. The line of intersection Se' is a line of intersection between the sphere S and a circular cone which has a line X' inclined from the reference axis X by the angle $\beta$ as the central line, and has the center O of the sphere S as the center, and whose curved surface coincides with the scattering direction of the diffracted light components. FIG. 9B is a projection view of the spatial distribution of the diffracted light components De1' to De4' on the sphere S when viewed from the direction of the line n onto the equatorial plane. In FIG. 9A, points Ed' and St' represent intersections between the line of intersection Se' and the substrate 15. An angle $\theta_{01}$ represents an exit angle of regularly reflected light. In this case, the exit angle corresponds to a spatial angle in a direction from the intersection St' toward the intersection Ed'.

As shown in FIGS. 8A to 9B, diffracted light components produced from a repetitive parallel pattern having periodicity in only one direction has a simple spatial distribution.

Cases will be examined below with reference to FIGS. 10A to 11B wherein the pattern A1 in FIG. 8A and the pattern A2 shown in FIG. 9A are respectively isolated patterns. An isolated pattern, the longitudinal direction of which extends in a direction parallel to the reference axis X, as shown in FIG. 10A, is represented by B1, and an isolated pattern, the longitudinal direction of which extends in a direction parallel to the reference axis X', as shown in FIG. 11A, is represented by B2. Like in FIG. 9A, the axis X' is inclined from the X axis by the angle $\beta$. Paying attention to the scattering direction of diffracted light components, planes including the principal rays from the isolated patterns B1 and B2 respectively coincide with planes including the principal rays of discrete diffracted light components from the repetitive patterns A1 and A2 shown in FIGS. 8A and 9A. As shown in normal projection views of FIGS. 10B and 11B of the diffracted light distribution on the sphere S when viewed from the direction of the line n onto the equatorial plane, diffracted light components from the pattern B1 are distributed on the line of intersection Se, and diffracted light components from the pattern B2 are distributed on the line of intersection Se'. However, the spatial distribution of the isolated pattern does not define a discrete pattern, but defines a continuous diffraction cone.

A case has been described wherein a simple pattern is formed on a substrate. However, a pattern formed on a substrate as a presently used IC circuit pattern is defined by, e.g., lines forming angles of 0°, 30°, 45°, 90°, and the like with respect to the reference coordinate axis X. In this manner, since an actual circuit pattern is formed by overlapping various circuit patterns, various patterns are available, and the distribution of diffracted light components to be produced is complicated.

A circuit pattern having a plurality of periodicities will be described below.

For example, when a repetitive rectangular pattern C1 having aligning directions in both the reference coordinate axes X and Y is present, as shown in FIG. 12A, it has periodicities in two directions, i.e., in the X and Y directions. A case will be examined wherein light I is radiated on this pattern. Diffracted light components from the pattern C1 are distributed on intersections between two different arrays of lines of intersection, i.e., the array of lines of intersection in the X direction ($X_1$ to $X_5$) and the array of lines of intersection in the Y direction ($Y_1$ to $Y_5$) on the sphere S. FIG. 12A illustrates only the line of intersection $X_3$ as one of the array of lines of intersection in the X direction, and the line of intersection $Y_3$ as one of the array of lines of intersection in the Y direction of these arrays of lines of intersection. FIG. 12B shows a distribution of diffracted light components when viewed from the direction of the line n. As shown in FIG. 12B, the diffracted light components are distributed on the intersections between the array of lines of intersection in the X direction ($X_1$ to $X_5$) and the array of lines of intersections in the Y direction ($Y_1$ to $Y_5$) on the normal projection view onto the equatorial plane. In the case of the pattern C1, the diffracted light distribution on the normal projection view has a period parallel to the X direction, and a period parallel to the Y direction.

The principle of discriminating foreign matter from a circuit pattern according to the present invention will be described after a description of the fact that almost no output difference appears among light-receiving elements between foreign matter and a circuit pattern with reference to the strength distribution of diffracted light.

The strength distributions of diffracted light components on the sphere S shown in FIGS. 8A, 9A, and 12A will be examined below with reference to FIGS. 13A and 13B. In FIGS. 13A and 13B, the strength of diffracted light is plotted along the ordinate, and an exit angle $\theta$ is plotted along the abscissa. $\gamma$ represents the angular aperture of incident light I, $\alpha$ represents the incident angle of the incident light I, and $\delta$ represents the pitch of adjacent diffracted light components (a minimum spatial angle defined between diffracted light components in a plane including the optical axes of at least two discrete diffracted light components produced in a predetermined direction).

On the sphere S, the strength is maximized at the point Re where the 0th-order diffracted light component passes in any of the above-mentioned patterns A1, A2, and C1, and the strength is generally weakened as the diffracted light component is separated from the point Re. The strength distribution of diffracted light components from the pattern A1 having a relatively low degree of miniaturization shown in FIGS. 8A and 8B will be examined below as a simple example. The strength distribution in this case forms a mountain-like strength distribution pattern having the direction of the 0th-order diffracted light component (direction of the point Re) as a maximum peak, as shown in FIG. 13B, if the exit angle $\theta$ on the line of intersection (the spatial angle on the line of intersection) is used as a parameter. As the exit angle $\theta$ is separated from $\theta_0$ as the direction of the 0th-order diffracted light component, the strength tends to be decreased. In the conventional detecting apparatus shown in FIG. 17, the light-receiving elements are arranged at positions separated from $\theta_0$ and corresponding to a sufficiently decreased strength distribution so as to avoid the influence of the 0th-order light, and to perform detection at a maximum reception sensitivity.

Subsequently, a circuit pattern similar to the circuit pattern A1 shown in FIG. 8A, and having a smaller line width than that of the pattern shown in FIG. 8A will be examined below. The spatial strength distribution of diffracted light components in this case is as shown in FIG. 13A, and the pitch $\delta$ of diffracted light components is increased. In addition, the strength is not so weakened as the exit angle $\theta$ is separated from the direction $\theta_0$ of 0th-order light. For this reason, when the circuit pattern C1 having a plurality of periodic directions shown in FIG. 12A is miniaturized, the spatial distribution of diffracted light components from the circuit pattern C1 macroscopically approaches isotropic directivity. Therefore, when the circuit pattern A1 or C1 shown in FIG. 8A or 12A is miniaturized, the existing foreign particle detecting apparatus shown in FIG. 17 cannot discriminate scattered light components from foreign matter from diffracted light components from the circuit pattern A1 or C1.

Thus, in the foreign particle detecting apparatus according to the present invention, foreign matter can be discriminated from a circuit pattern depending on whether or not scattered light components from an object to be detected are spatially discrete light components.

The principle of the present invention will now be described. As shown in FIGS. 8A to 9B and FIGS. 12A and 12B, when spatially discrete diffracted light components are produced, the angular apertures of the respective diffracted light components can be regarded to be substantially constant, and are almost equal to the angular aperture $\gamma$ of the incident light I.

As described above, when the circuit pattern is miniaturized, the pitch $\delta$ of diffracted light components is increased as the pitch of the pattern is decreased, as shown in FIG. 13A. In other words, the degree of spatial discreteness is increased. According to the present invention, whether or not the spatial distribution of diffracted light components is discrete is discriminated using at least two light-receiving means (light-receiving elements).

The principle of the present invention will be described in more detail with reference to FIGS. 14A to 16D. In FIGS. 14A to 16D, the strength of diffracted light from a circuit pattern and the strength of scattered light from foreign matter are plotted along the ordinate, and the spatial angle is plotted along the abscissa. In FIGS. 14A to 16D, D, E, F, G, H, J, and K represent light-receiving elements, and $D_0$, $D_1$, $D_2$, and $D_3$ represent angular apertures of the light-receiving elements. Pitches $\delta_0$, $\delta_1$, $\delta_2$, $\delta_3$, $\delta_4$, $\delta_5$, $\delta_6$, $\delta_7$, and $\delta_8$ represent those of diffracted light components. In this case, the angular aperture of diffracted light is almost equal to the angular aperture $\gamma$ of incident light I. In the following description, light-receiving optical systems of the light-receiving elements will be disregarded, and light from a substrate is assumed to become directly incident on the light-receiving elements.

A case will be described below wherein foreign matter is discriminated from a circuit pattern using two light-receiving elements. As shown in FIGS. 14A to 14D, the two light-receiving elements D and E are arranged to be separated so that a spatial angle $\Psi$ defined between the two light-receiving elements D and E (to be simply referred to as an "angle $\Psi$ defined between the light-receiving elements" hereinafter) is substantially equal to an angular aperture $\gamma$ of incident light I. The angle $\Psi$ is a minimum spatial angle defined between the light-receiving elements. FIGS. 14A to 14C show states of diffracted light components distributed on different lines of intersection (including a case wherein a circuit pattern is different). The angular apertures of these diffracted light components are almost equal to $\gamma$. FIG. 14A shows a case wherein one of diffracted light components passes between the two light-receiving elements D and E, and diffracted light is incident on neither of the two light-receiving elements D and E. FIG. 14B shows a case wherein one of diffracted light components is incident on the light-receiving element E, and no diffracted light is incident on the light-receiving element D. FIG. 14C shows a case wherein the pitch $\delta_2$ of the diffracted light components is equal to or larger than the maximum spatial angle $(2D_1+\gamma)$ between the two light-receiving elements, and diffracted light is incident on neither of the two light-receiving elements D and E. FIG. 14D shows scattered light components from foreign matter. In FIG. 14D, scattered light components are incident on both the two light-receiving elements D and E.

Photoelectric signals from these two light-receiving elements are binarized, and their logical products are calculated.

TABLE 1

| Pattern | D Output | E Output | D × E |
|---|---|---|---|
| ① | 0 | 0 | 0 |
| ② | 0 | 1 | 0 |
| ③ | 0 | 0 | 0 |
| Foreign Matter | 1 | 1 | 1 |

As shown in Table 1 (truth table), discrete diffracted light components from the patterns yield D×E=0, and continuous scattered light components from foreign matter yield D×E=1. Therefore, foreign matter can be discriminated from a circuit pattern on the basis of the signals from the two light-receiving elements.

Note that the pitches $\delta_0$, $\delta_1$, and $\delta_2$ of diffracted light components when the diffracted light components are as shown in FIGS. 14A to 14C depend on the circuit patterns.

As described above, when foreign matter is discriminated from the circuit pattern using the two light-receiving elements D and E, the following two conditions I and II must be satisfied:

I. The minimum spatial angle $\Psi$ defined between the two light-receiving elements D and E is substantially equal to or slightly larger than the angular aperture $\gamma$.

II. The maximum spatial angle defined between the two light-receiving elements D and E is equal to or smaller than the pitch of diffracted light components.

The conditions I and II can be expressed by the following relation (1):

$$\delta \geq Res(n = 2) = \gamma + 2D_1 \quad (1)$$

$\begin{cases} Res(n = 2): & \text{resolution of diffracted light by two} \\ & \text{light-receiving elements } D \text{ and } E \\ \delta: & \text{pitch of diffracted light} \\ D_1: & \text{angular aperture of light-receiving} \\ & \text{elements } D \text{ and } E \\ \gamma: & \text{angular aperture of incident light } I \end{cases}$ As can be understood from relation (1), when $D_1$ is decreased, diffracted light resolution can be increased, and the limit of the increase in resolution is $Res(n=2)=\gamma$ when $D_1\simeq 0$.

In any of FIGS. 14A to 14C, when the light-receiving elements are arranged to satisfy the conditions I and II, spatially discrete diffracted light components produced at the angular aperture $\gamma$, and at the pitches $\delta_0$, $\delta_1$, and $\delta_2$ are incident on either of the light-receiving elements. In contrast to this, spatially continuous scattered light components produced from foreign matter are incident on both the light-receiving elements D and E. Thus, as described above, foreign matter can be discriminated from the circuit pattern.

Even when the angle $\Psi$ defined between the light-receiving elements is slightly larger than the angular apertures $\gamma$, discrimination is possible as long as a condition $\delta \geq Res(n=2)=\Psi+2D_1$ is satisfied. However, it is advantageous in terms of resolution to set the angle defined between the light-receiving elements to be substantially equal to the angular aperture $\gamma$.

A case will be described below wherein foreign matter is discriminated from a circuit pattern using three light-receiving elements. As shown in FIGS. 15A to 15D, the light-receiving elements F, G, and H are arranged, so that the angle $\Psi$ defined between the light-receiving elements F and H is set to be substantially equal to the angular aperture $\gamma$ of incident light I. The light-receiving elements F and H are those located at two ends of the array of the three light-receiving elements F, G, and H. FIGS. 15A to 15C show diffracted light components distributed at pitches $\delta_3$, $\delta_4$, and $\delta_5$ smaller than the pitches $\delta_0$, $\delta_1$, and $\delta_2$ of diffracted light components shown in FIGS. 14A to 14C. FIG. 15A shows a case wherein diffracted light is located between the two light-receiving elements F and N, and a diffracted light component is incident on only the light-receiving element G. FIG. 15B shows a case wherein one of diffracted light components is incident on the light-receiving element H, and no diffracted light components are incident on the light-receiving elements F and G. FIG. 15C shows a case wherein the pitch $\delta_5$ is equal to or larger than the maximum spatial angle $(D_2+\gamma)$ between the two light-receiving elements (F and G; G and H), and no diffracted light component is incident on one of the light-receiving elements F, G, and H. FIG. 15D shows scattered light components from foreign matter, and shows a case wherein scattered light components are incident on all the three light-receiving elements F, G, and H. The truth table in this case is shown in Table 2-a below.

TABLE 2-a

| Pattern | F Output | G Output | H Output | F × G × H |
|---|---|---|---|---|
| ①' | 0 | 1 | 0 | 0 |
| ②' | 0 | 0 | 1 | 0 |
| ③' | 1 | 0 | 1 | 0 |
| Foreign Matter | 1 | 1 | 1 | 1 |

As described above, when the three light-receiving elements F, G, and H are used, foreign matter can be discriminated from the circuit pattern without changing the angular apertures of the light-receiving elements even when the pitch $\delta$ of diffracted light is decreased.

As described above, when foreign matter is discriminated from a circuit pattern using the three light-receiving elements F, G, and H, the following two conditions III and IV must be satisfied.

III. The minimum spatial angle $\Psi$ defined between the two light-receiving elements F and H located at the two ends is substantially equal to or slightly larger than the angular aperture $\gamma$.

IV. The maximum spatial angle defined between the two adjacent light-receiving elements (F and G; G and H) is equal to or smaller than the pitch of diffracted light components.

When the angular apertures of the light-receiving elements are decreased, discrimination performance equivalent to or more than that obtained when the light-receiving elements F, G, and H are aligned in an array can be provided. This case will be explained below using two light-receiving elements J and K shown in FIGS. 15A to 15D. FIG. 15A shows a case wherein one of diffracted light components passes between the two light-receiving elements J and K, and diffracted light, is incident on neither of the two light-receiving elements J and K. FIG. 15B shows a case wherein one of diffracted light components is incident on the light-receiving element K, and no diffracted light is incident on the light-receiving element J. FIG. 15C shows a case wherein the pitch $\delta_5$ of the diffracted light components is equal to or larger than the maximum spatial angle $(2D_3+\gamma)$ between the two light-receiving elements, and diffracted light is incident on neither of the two light-receiving elements J and K. FIG. 15D shows scattered light components from foreign matter, and shows a case wherein scattered light components are incident on both the two light-receiving elements J and K.

The truth table in this case is shown in Table 2-b below, and foreign matter can be discriminated from the circuit pattern, as shown in Table 2-b.

TABLE 2-b

| Pattern | J Output | K Output | J × K |
|---|---|---|---|
| ① | 0 | 0 | 0 |
| ② | 0 | 1 | 0 |
| ③ | 1 | 0 | 0 |
| Foreign Matter | 1 | 1 | 1 |

Furthermore, as shown in FIGS. 16A to 16D, when the angular aperture of three light-receiving elements is decreased, discrimination performance between foreign matter and a circuit pattern can be improved. FIGS. 16A to 16D show a case wherein pitches $\delta_6$, $\delta_7$, and $\delta_8$ are decreased to be equal to about the angular aperture $\gamma$, i.e., wherein the angular aperture of each of the light-receiving elements L, M, and N is set to be $D_0 = \gamma/3$. FIG. 16A shows a case wherein diffracted light is located between the two light-receiving elements L and N, and a diffracted light component is incident on only the light-receiving element M. FIG. 16B shows a case wherein one of diffracted light components is incident on the light-receiving elements M and N, and no diffracted light component is incident on the light-receiving element L. FIG. 16C shows a case wherein the pitch $\delta_8$ of diffracted light components is equal to or larger than the maximum spatial angle $(D_0+\gamma)$ between the two light-receiving elements (L and M; M and N), and no diffracted light component is incident on the light-receiving element M. FIG. 16D shows scattered light components from foreign matter, and shows a case wherein the scattered light components are incident on all the three light-receiving elements L, M, and N. The truth table in this case is shown in Table 3 below. As shown in Table 3, foreign matter can be discriminated from a circuit pattern.

TABLE 3

| Pattern | L Output | M Output | N Output | L × M × N |
|---|---|---|---|---|
| ④ | 0 | 1 | 0 | 0 |
| ⑤ | 0 | 1 | 1 | 0 |
| ⑥ | 1 | 0 | 1 | 0 |
| Foreign Matter (small) | 1 | 1 | 1 | 1 |

Therefore, foreign matter can be discriminated from a pattern with higher diffracted light resolution than in a case wherein two light-receiving elements are juxtaposed. In this case, it is advantageous in terms of resolution to set the minimum angle defined between the light-receiving elements located at the two ends to be substantially equal to the angular aperture $\gamma$ of incident light I, and is also advantageous to satisfy conditions for the pitches and the resolution.

In general, when n light-receiving elements having the same angular aperture $D_0$ are used, an angle $\Psi$ formed between two light-receiving elements located at the two ends is set to be substantially equal to the angular aperture $\gamma$ of incident light I, and the remaining $(n-2)$ light-receiving elements are arranged at equal intervals in the angular aperture $\gamma$, diffracted light resolution Res(n) is given by equation (2), and $\delta \geq \text{Res}(n)$ must be satisfied to discriminate diffracted light components.

$$Res(n) = 2D_0 + \frac{[\gamma - (n-2)D_0]}{(n-1)} \quad (2)$$

If $n=2$ is substituted in equation (2), relation (1) can be obtained.

As described above, FIGS. 16A to 16D show a case wherein the three light-receiving elements L, M, and N are arranged, and $n=3$ and $D_0=\gamma/3$ are substituted in equation (2). The resolution Res(n=3) is $\gamma$ from equation (2), and the limit of the diffracted light resolution is $\gamma/2$ when $D_0=0$.

As shown in FIGS. 16A to 16D, the pitch of diffracted light components is decreased to be equal to or smaller than the angular aperture $\gamma$, and the strength of diffracted light is decreased when a circuit pattern has a low degree of discreteness, as shown in, e.g., FIG. 13B. When the strength of scattered light components from foreign matter is larger than that of diffracted light components, the light-receiving elements are arranged near an incident point of incident light (a portion where the strength of diffracted light is low) like in the conventional foreign particle detecting apparatus, thus discriminating foreign matter from a circuit pattern. However, when smaller foreign matter is to be detected near the incidence point, the strength of scattered light from foreign matter is also decreased, and foreign matter cannot be discriminated from a circuit pattern by the conventional foreign particle detecting apparatus.

However, as described above, when three or more light-receiving elements are arranged to decrease diffracted light resolution to be equal to or lower than $\gamma$, small foreign matter can be discriminated from a circuit pattern having a low degree of discreteness. The reason why the discrimination is possible is that the present invention discriminates foreign matter from a circuit pattern not on the basis of the strength difference between diffracted light from the circuit pattern and scattered light from foreign matter, but on the basis of the difference in degree of spatial discreteness.

In this manner, when the diffracted light resolution is increased, weak diffracted light produced from the circuit pattern can be discriminated from weak scattered light produced from small foreign matter.

As described above, according to the present invention, foreign matter can be discriminated from a circuit pattern with high resolution on the basis of whether or not scattered light components from a miniaturized circuit pattern are spatially discrete, and small foreign matter attached onto a surface to be detected on which a circuit pattern which has periodicity not only in one direction but also in many directions can be detected. Furthermore, when the angular width of light incident on the light-receiving elements, and the number of light-receiving elements are optimized in correspondence with the size of foreign matter to be detected or a circuit pattern, a foreign particle detecting apparatus having a desired performance can be constituted.

BRIEF DESCRIPTION OF THE DRAWINGS

FIGS. 14A to 14D, FIGS. 15A to 15D, and FIGS. 16A to 16D are views showing the principle of discriminating diffracted light from a pattern from scattered light from foreign matter.

DESCRIPTION OF THE PREFERRED EMBODIMENTS

Figure 1:
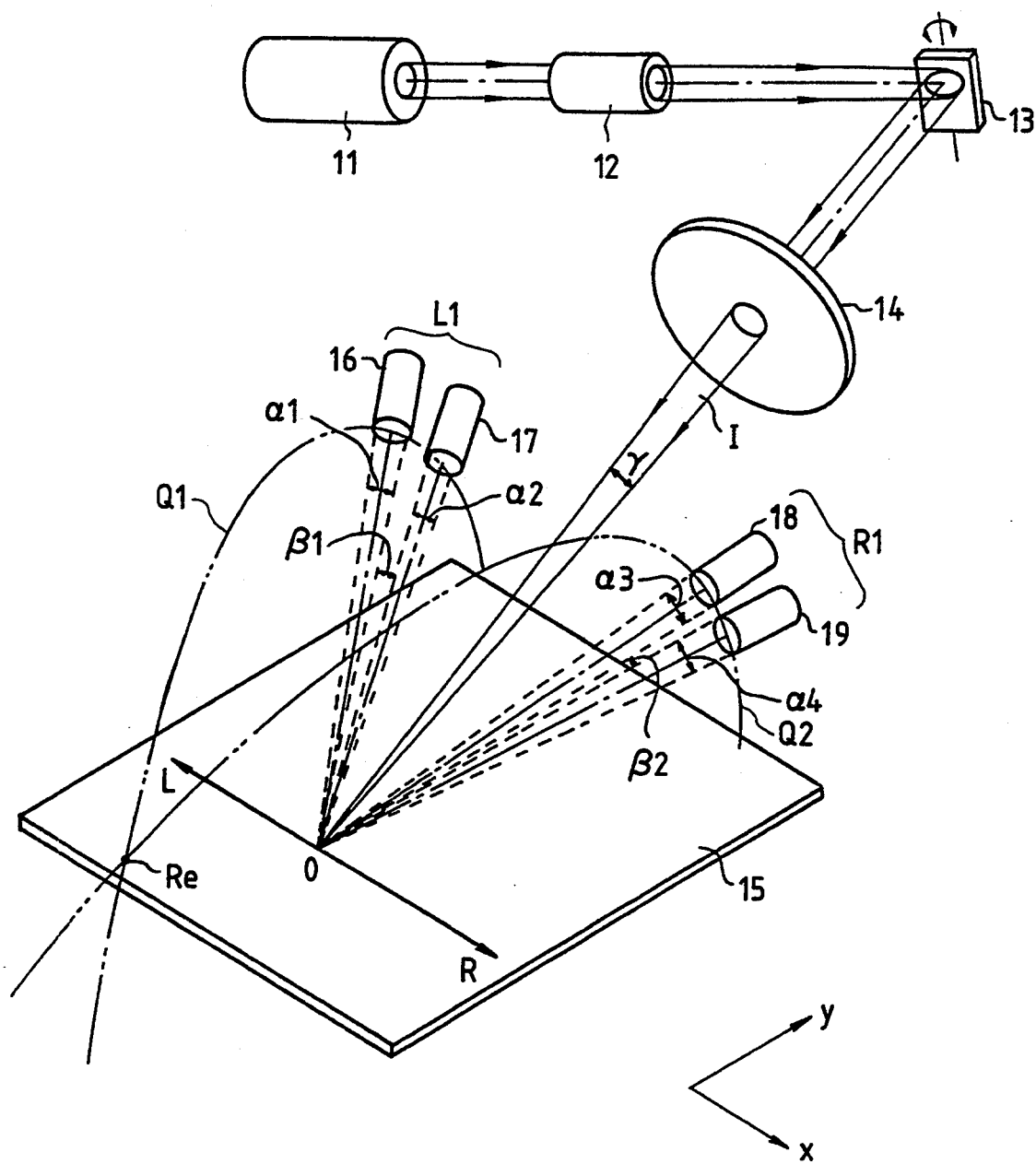
FIG. 1 is a perspective view showing an arrangement of the first embodiment of the present invention.
Figure 2:
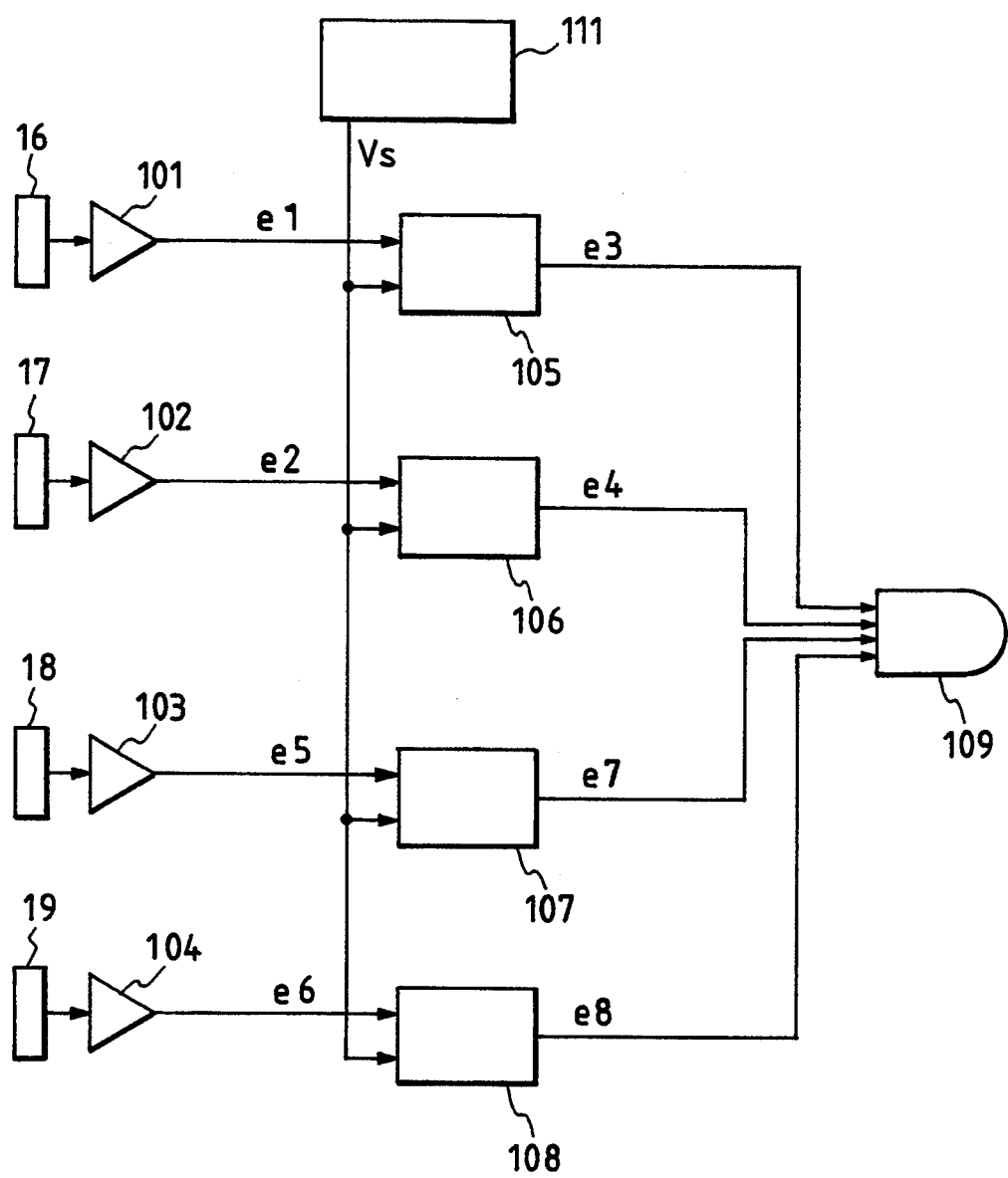
FIG. 2 is a diagram showing a detection circuit suitable for the first embodiment of the present invention.

FIG. 1 is a perspective view showing an arrangement of the first embodiment of the present invention, and FIG. 2 is a diagram showing a detection circuit suitable for the arrangement shown in FIG. 1.

In FIG. 1, coherent light emitted from a laser light source 11 is focused on a substrate 15 at an angular aperture $\gamma$ via a beam expander 12, a vibration mirror 13 constituting a moving means for moving the light relative to the substrate 15 (a reticle, wafer, or the like) on which a circuit pattern is formed, and an f-$\theta$ lens 14 constituting a focusing lens for focusing the light onto the substrate 15. In this case, incident light I is focused on the substrate 15 at a predetermined incident angle. The focused incident light I is optically scanned along a scanning line L-O-R (X direction) upon vibration of the vibration mirror 13. The f-$\theta$ lens 14 is a lens having a relatively long focal length, and decreases a vibration angle on the substrate 15. The substrate 15 is placed on a stage (not shown) which is movable in the Y direction. Thus, foreign matter can be detected over the entire surface of the substrate 15.

Figure 4A:
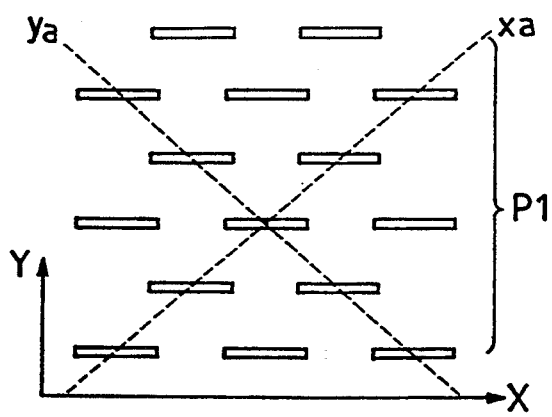
FIG. 4A shows a circuit pattern having two periodic directions inclined at an equal angle with respect to the X direction.
Figure 8A:
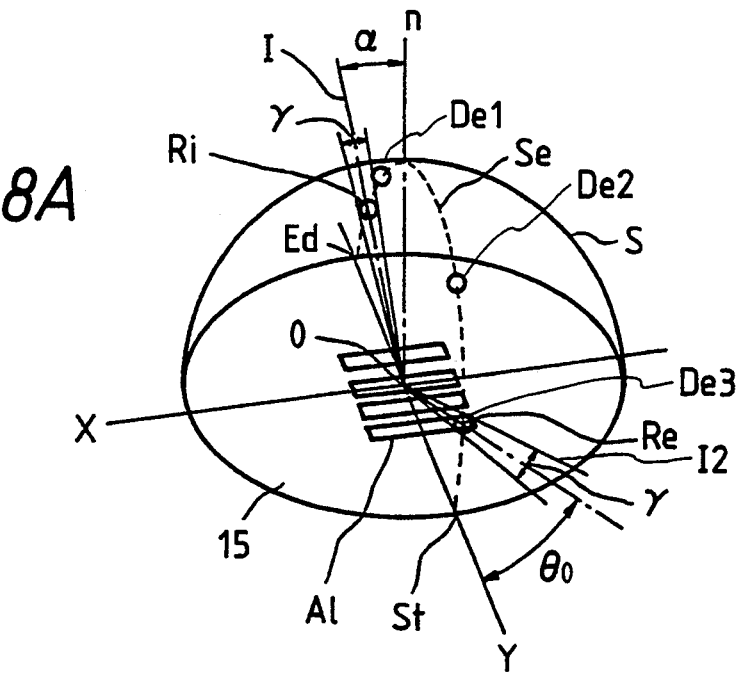
FIG. 8A shows a repetitive pattern.
Figure 8B:
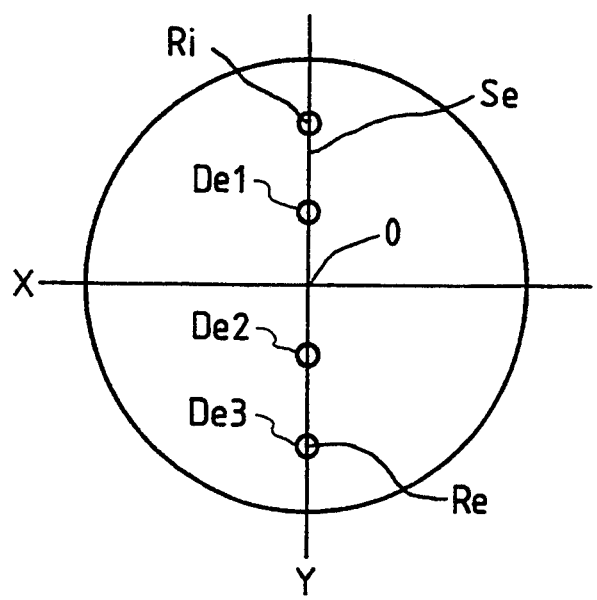
FIG. 8B is a normal projection view showing the distribution of diffracted light components from the pattern shown in FIG. 8A.
Figure 9A:
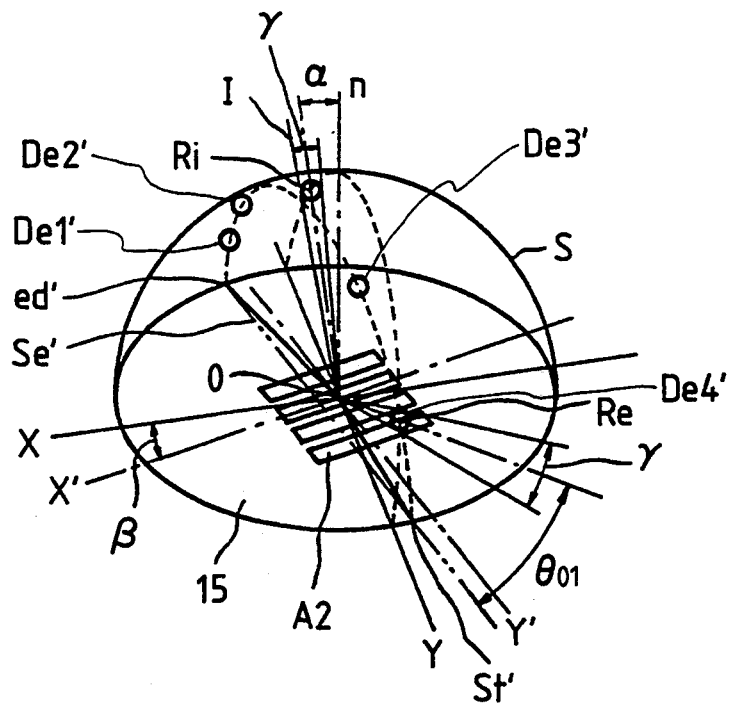
FIG. 9A shows a repetitive pattern having a periodic direction in a direction inclined with respect to a plane of incidence.
Figure 9B:
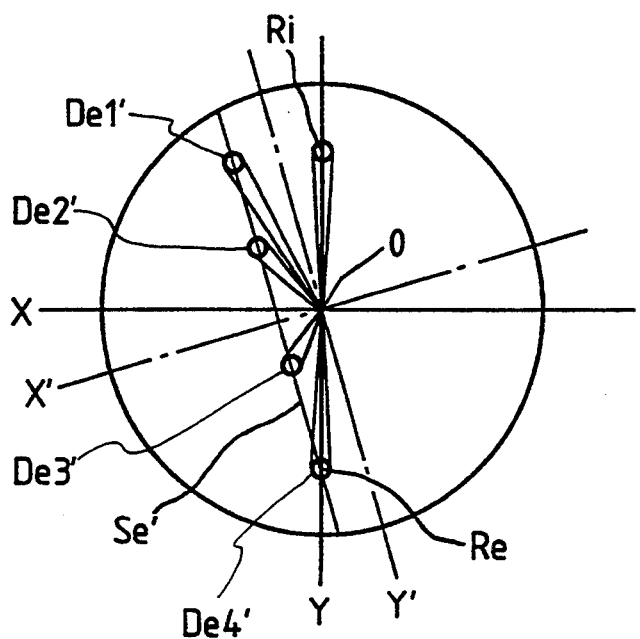
FIG. 9B is a normal projection view showing the distribution of diffracted light components from the pattern shown in FIG. 9A.

Assume that a miniaturized circuit pattern P1 having periodicity shown in FIG. 4A is formed on the substrate 15. When the incident light I is radiated on the circuit pattern P1, the pattern P1 produces discrete diffracted light components. The circuit pattern P1 is often employed in a high-integration LSI such as a DRAM, and is a circuit pattern having two periodic directions in Xa and Ya directions defining an equal angle $\theta_P$ with respect to the reference X direction of the substrate therebetween. Diffracted light components produced upon incidence of the incident light I onto the substrate 15 having the circuit pattern P1 are distributed on lines of intersection Q1 and Q2 (corresponding to the line Se in FIGS. 8A and 8B). A detection means L1 including light-receiving elements 16 and 17 is arranged on the line of intersection Q1, and a detection means R1 including light-receiving elements 18 and 19 is arranged on the other line of intersection Q2. In order to prevent the influence of the 0th-order diffracted light component of diffracted light components, the detection means L1 and R1 are arranged at a position far from the propagation direction of the 0th-order diffracted light component, i.e., near the f-$\theta$ lens 14. The light-receiving surfaces of the light-receiving elements (16 and 17; 18 and 19) are assumed to be located on tangents to the lines of intersection Q1 and Q2. Note that the angular aperture $\gamma$ of the incident light I is determined by the characteristics of the f-$\theta$ lens 14. For this reason, the angular aperture $\gamma$ can be determined in advance. An angle $\beta 1$ defined between the light-receiving elements 16 and 17 is set to be substantially equal to the angular aperture $\gamma$. If the angular apertures of these two light-receiving elements (the angular apertures of reception light components) are respectively represented by $\alpha 1$ and $\alpha 2$, the maximum angle $(\alpha 1 + \beta 1 + \alpha 2)$ defined between the two light-receiving elements is set to be equal to or smaller than the pitch (corresponding to $\delta$ in FIGS. 14A to 14D) of adjacent diffracted light components distributed on the line of intersection, and satisfies the above-mentioned conditions I and II. The angular apertures of the light-receiving elements 18 and 19 of the detection means R1 are respectively represented by $\alpha 3$ and $\alpha 4$, and an angle $\beta 2$ is defined between the two light-receiving elements 18 and 19. The detection means R1 is arranged in the same manner as the means L1. Discrimination between a pattern and foreign matter can be performed using one of the detection means L1 and R1. However, in order to increase detection precision, the detection means are arranged at two positions.

The angle $\beta 1$ or $\beta 2$ defined between the two light-receiving elements (16 and 17; 18 and 19) when the beam spot position of the incident light I is located at the center O on the scanning line is substantially equal to the angular aperture $\gamma$ of the incident light I. However, when the beam spot position falls outside the center O on the scanning line, the angular aperture $\gamma$ of the incident beam I is decreased. In this case, discrimination will not be disturbed as long as the above-mentioned conditions I and II are satisfied. However, when a small variation caused by mirror scanning is to be prevented, the vibration mirror 13 is constituted as a stationary mirror, and the light I is moved relative to the substrate 15 upon movement of the stage so as not to incline the light I with respect to the scanning line L-O-R. Alternatively, the f-$\theta$ lens 14 may be constituted as a telecentric optical system, so that light can be incident on the substrate 15 at a predetermined angle. The angular aperture of diffracted light becomes slightly smaller than the angular aperture $\gamma$ of the incident light I near the f-$\theta$ lens 14 or positions other than a position near a position where the 0th-order diffracted light component is produced. However, discrimination will not be disturbed as long as the above-mentioned conditions I and II are satisfied. The angular aperture of diffracted light components near a position where the light-receiving elements are arranged may be actually measured to determine an angle defined between the light-receiving elements (16 and 17; 18 and 19).

In the above description, the light-receiving elements are arranged on the lines of intersection. However, the present invention is not limited to this. For example, an imaginary line of intersection may be considered between lines of intersection although no diffracted light components are distributed thereon, and the light-receiving elements may be arranged on the imaginary line of intersection.

Figure 10A:
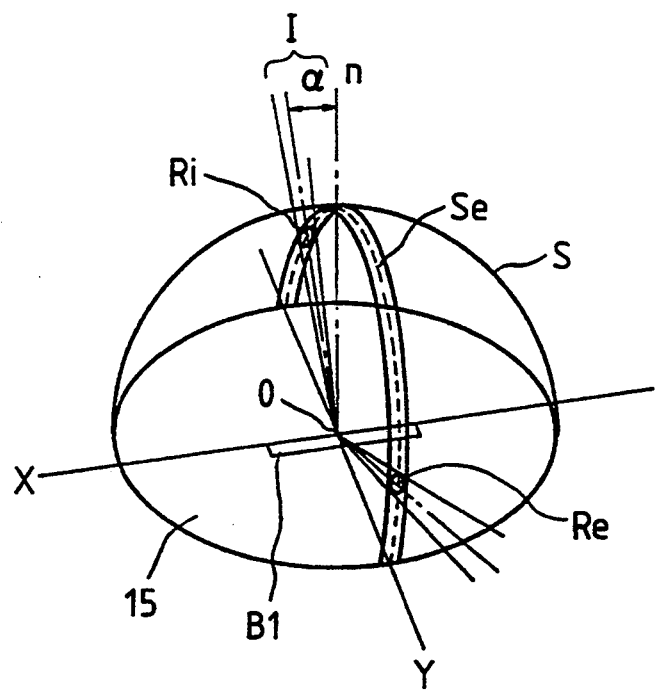
FIG. 10A shows an isolated pattern.
Figure 10B:
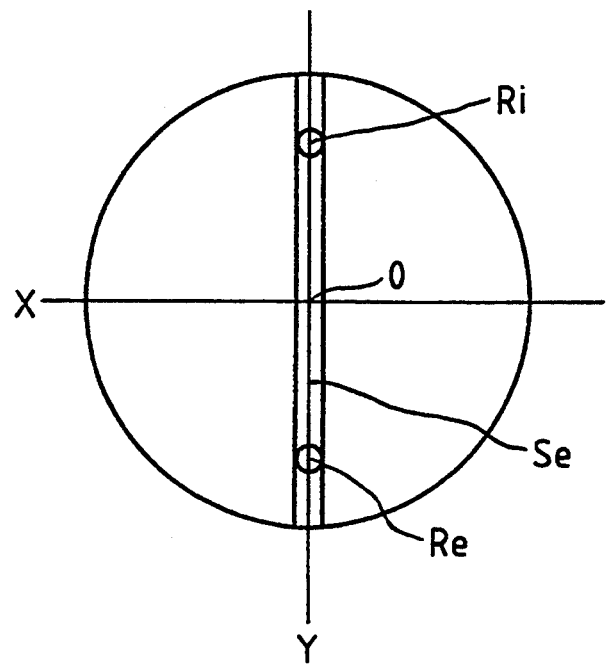
FIG. 10B is a normal projection view showing the distribution of diffracted light components from the pattern shown in FIG. 10A.
Figure 11A:
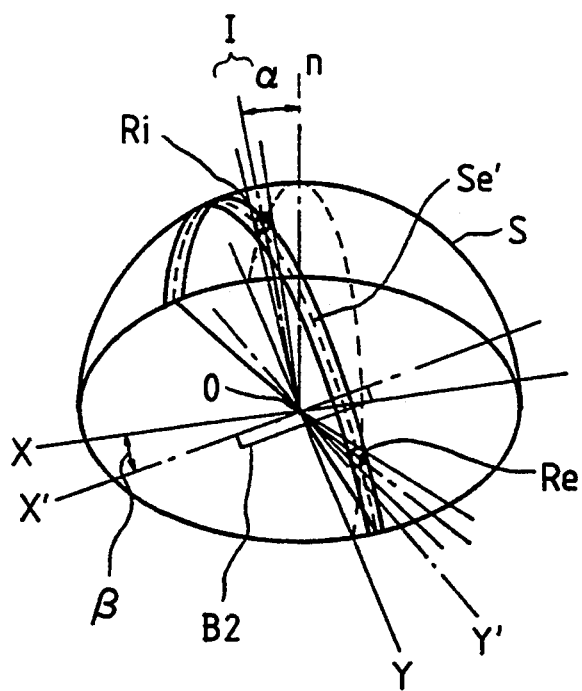
FIG. 11A shows an isolated pattern inclined with respect to a plane of incidence.
Figure 11B:
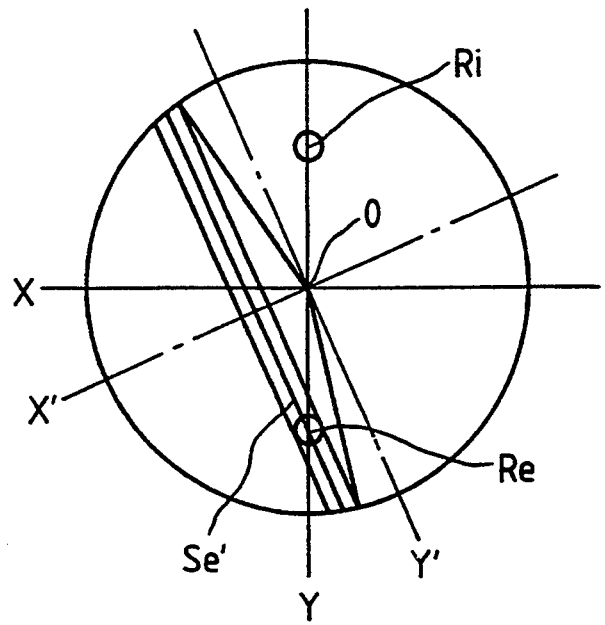
FIG. 11B is a normal projection view showing the distribution of diffracted light components from the pattern shown in FIG. 11A.

In the above embodiment, a pattern having periodicity has been described. In addition to such a pattern, non-periodic patterns having various directivities may be present. In this case, diffracted light having a continuous spatial distribution similar to that of a diffraction cone from an isolated pattern shown in FIGS. 10A and 10B is produced. However, the direction in which the diffraction cone is produced is limited by the directivity of the circuit pattern. For this reason, when the light-receiving elements can be arranged at positions avoiding the position of the diffraction cone, foreign matter can be discriminated from the circuit pattern on the basis of whether or not diffracted light incident on the light-receiving element is discrete even when the diffraction cone is present.

A signal processing system will be described below with reference to FIG. 2.

Photoelectric signals from the light-receiving elements 16 and 17 are respectively input to amplifiers 101 and 102. Amplified signals e1 and e2 are respectively input to comparators 105 and 106. The other input of each comparator is applied with a slice voltage Vs from a slice level generator 111. The comparators 105 and 106 respectively compare the voltage values of the signals e1 and e1 with the slice voltage Vs. When the voltage values of the signals e1 and e2 are larger than the slice voltage Vs, the comparators 105 and 106 respectively output signals e3 and e4 to an AND gate 109. When the voltage values of the signals e1 and e2 are smaller than the slice voltage Vs, no signals are output from the comparators 105 and 106 to the AND gate 109. When the slice level Vs is adjusted by the slice level generator 111, the size of foreign matter to be detected can be set.

Similarly, photoelectric signals from the light-receiving elements 18 and 19 are respectively amplified by amplifiers 103 and 104, and amplified signals e5 and e6 are input to comparators 107 and 108. These signals are compared with the slice level Vs. When the signals e5 and e6 exceed the slice voltage Vs, signals e7 and e8 are output from the comparators 107 and 108 to the AND gate 109, respectively.

The AND gate 109 calculates a logical product of the signals e3, e4, e7, and e8 to discriminate foreign matter from a circuit pattern. When the light-receiving elements 16, 17, 18, and 19 are arranged under the above-mentioned predetermined conditions, spatially discrete diffracted light components from the circuit pattern are not simultaneously received by the light-receiving elements 16, 17, 18, and 19, and the calculation result yields 0. In contrast to this, spatially continuous scattered light components from foreign matter are simultaneously input to the light-receiving elements, and the calculation result yields 1. In this manner, foreign matter can be easily discriminated from the circuit pattern.

Figure 3:
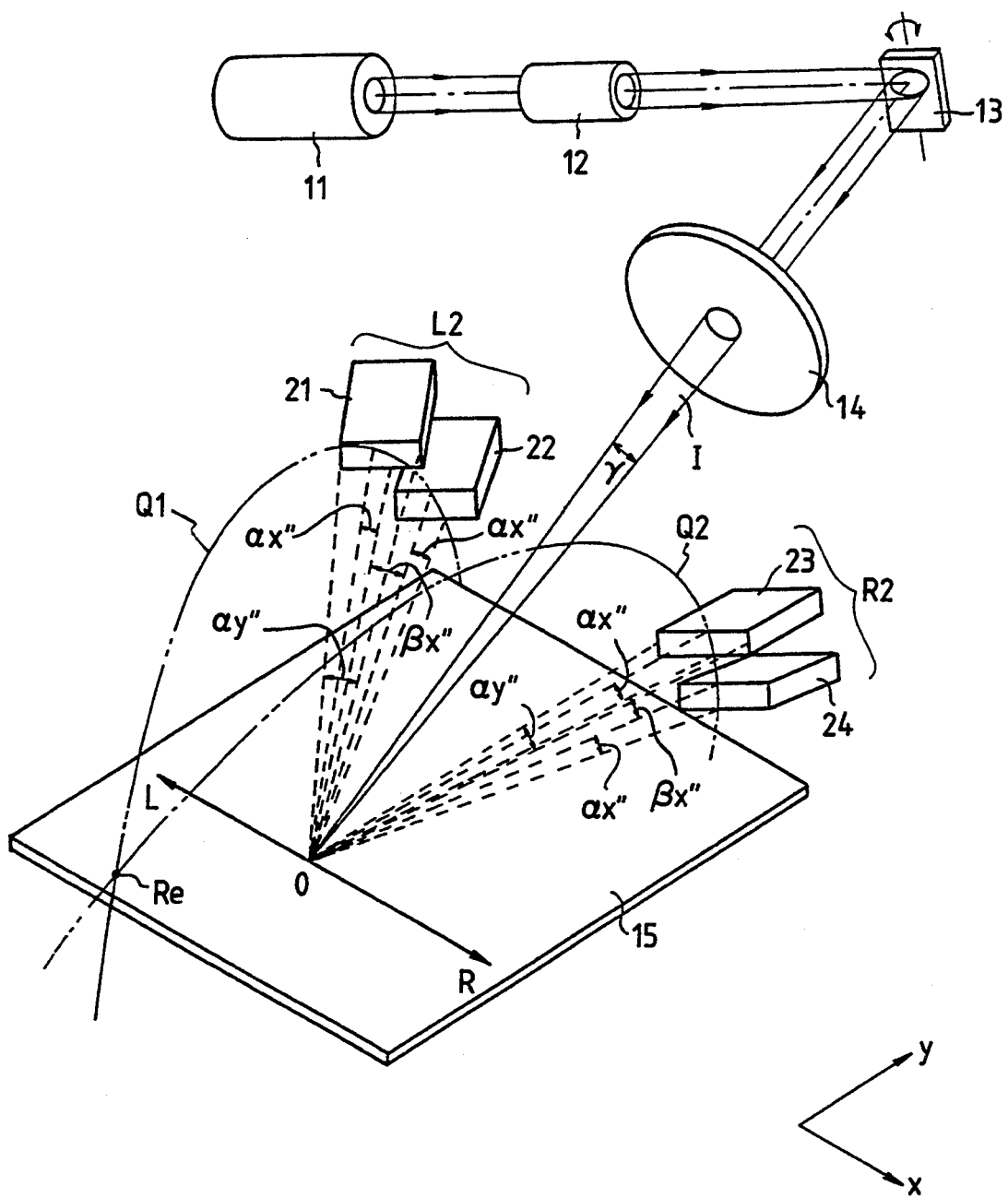
FIG. 3 is a perspective view showing an arrangement of the second embodiment of the present invention.
Figure 4B:
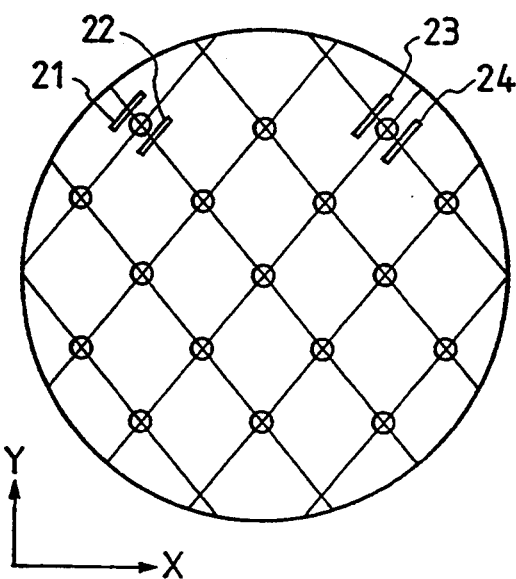
FIGS. 4B and 4C are projection views showing the distributions of diffracted light components from the pattern shown in FIG. 4A, and the arrangements of light-receiving elements.
Figure 4C:
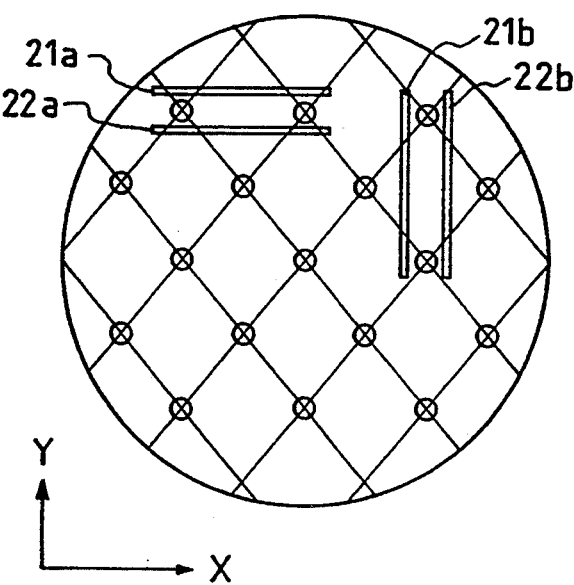
Figure 5A:
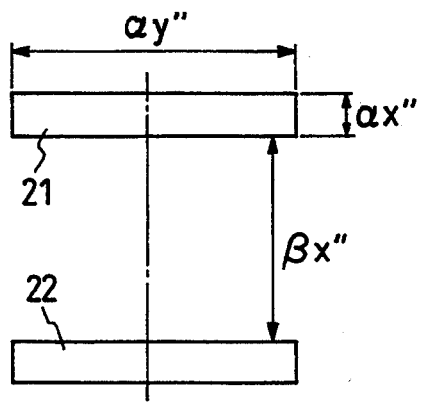
FIGS. 5A, 5B, 5C, and 5D are views showing the characteristic feature of light-receiving elements in the second embodiment of the present invention.

The second embodiment of the present invention will be described below with reference to FIG. 3. As an angular aperture $\alpha x''$ of a light-receiving element is smaller, discrimination performance (resolution) between a circuit pattern and foreign matter can be increased, as described above. In this embodiment, the angular aperture of the light-receiving element is decreased to increase detection sensitivity of foreign matter in consideration of this respect. In this embodiment, the shape of the light-receiving element (light-receiving surface) is changed from that in the first embodiment, and other arrangements and a discrimination method are the same as those in the first embodiment. The same reference numerals in this embodiment denote the same parts as in the first embodiment. Assume that light-receiving elements 21 and 22 constituting a detection means L2 and light-receiving elements 23 and 24 constituting a detection means R2 are respectively arranged on lines of intersection Q1 and Q2, and light-receiving surfaces are present on tangents to a sphere S. FIG. 5A is a view for explaining the feature and arrangement of the light-receiving elements 21 and 22 in FIG. 3. In FIGS. 5A to 5D, an x'' direction represents the directions of the above-mentioned lines of intersection Q1 and Q2, and a y'' direction represents a direction perpendicular to the x'' direction. In FIG. 5A, a minimum angle $\beta x''$ defined between the light-receiving elements in each detection means is substantially equal to an angular aperture $\gamma$ of incident light I. An angular aperture $\alpha x''$ in the x'' direction of each of the light-receiving elements 21 and 22 is set to be smaller than an angular aperture $\alpha y''$ in the y'' direction. This is to receive scattered light components from foreign matter on a sufficient area to increase the electrical S/N ratio while improving discrimination performance between a circuit pattern and foreign matter. A maximum angle ($\alpha x'' + \beta x'' + \alpha x''$) defined between the two light-receiving elements (21 and 22; 23 and 24) is set to be smaller than the pitch between adjacent diffracted light components distributed on the x" direction near a position where the light-receiving elements are arranged. FIG. 4B is a projection view showing the arrangement of the light-receiving elements 21 and 22. The light-receiving elements 23 and 24 are arranged to have the same relationship as described above. Note that FIGS. 4A–4C show the arrangement of the light-receiving elements on the normal projection view onto the equatorial plane.

Figure 5B:
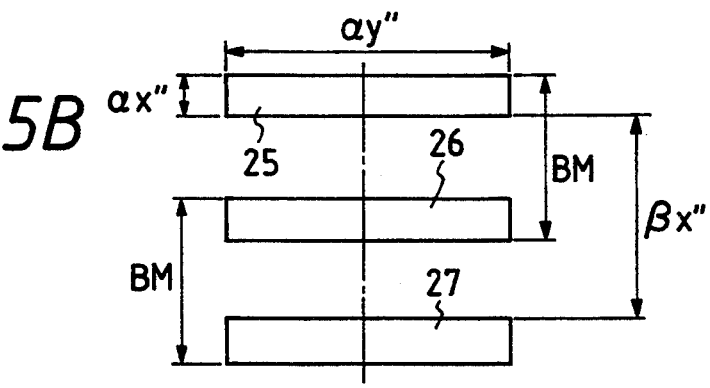

In order to further increase the discrimination resolution, the detection means L2 is constituted by three light-receiving elements 25, 26, and 27, as shown in FIG. 5B. In this case, the angular aperture $\alpha x''$ is set to be smaller than the angular aperture $\alpha y''$. In this manner, scattered light components from foreign matter are received on a sufficient area, and discrimination performance between a circuit pattern and foreign matter can be improved. Note that an angle $\beta x''$ defined between the light-receiving elements (25 and 27) located at the two ends is substantially equal to the angular aperture $\gamma$. A maximum angle BM defined between the adjacent light-receiving elements 25 and 26 or 26 and 27 is set to be equal to or smaller than the minimum pitch defined between adjacent diffracted light components. The detection means R2 is constituted to have the same positional relationship as described above. When the detection means comprising a combination of three light-receiving elements is employed, diffracted light discrimination performance which cannot be attained by the arrangement shown in FIG. 5A can be obtained since the condition given by equation (3) is satisfied as compared to the resolution obtained upon combination of two light-receiving elements:

$$\beta x''/3 > \alpha x'' \qquad (3)$$

In either of the detection means L2 and R2, signals from the three light-receiving elements are independently processed, and are input to the AND gate 109. Therefore, the AND gate 109 receives a maximum of six signals.

Figure 5C:
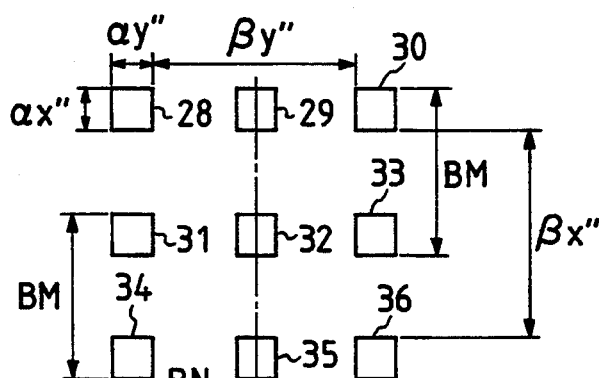
Figure 5D:
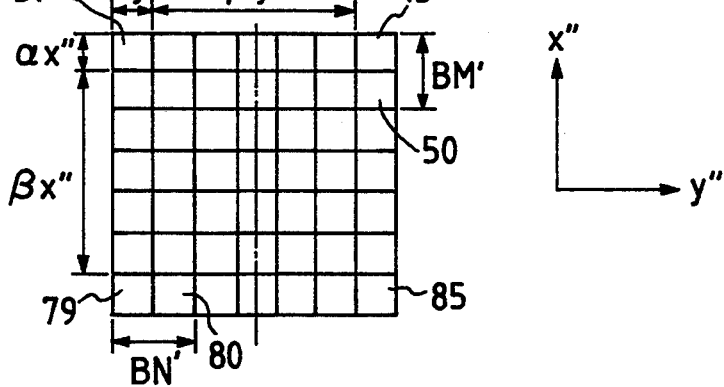

A modification of this embodiment will be described below with reference to FIGS. 5C and 5D. In the second embodiment, a method of increasing the resolution in the x" direction has been described. In the following modification, a method of improving detection precision by increasing resolution in the y" direction will be described below. The number of lines of intersections on which diffracted light components are distributed is not infinite, and diffracted light components have a degree of spatial discreteness in the y" direction, and have a pitch between adjacent diffracted light components in the y" direction. This modification pays attention to the degree of spatial discreteness in the y" direction.

Needless to say, when the light-receiving elements aligned in the x" direction, as shown in FIGS. 5A and 5B, are aligned in the y" direction, resolution in the y" direction can be obtained. In this case, a minimum angle defined between light-receiving elements (21 and 22; 25 and 27) located at the two ends in the y" direction must satisfy the same conditions as those described with reference to the x" direction, and is substantially equal to the angular aperture $\gamma$ of incident light I. A maximum angle defined between adjacent light-receiving elements (25 and 26; 26 and 27) is set to be equal to or smaller than the pitch between adjacent diffracted light components in the y" direction. In this manner, when resolution is provided in the y" direction, foreign matter can be discriminated from a pattern using diffracted light components spatially distributed in the y" direction while avoiding diffracted light components having a continuous spatial strength distribution like the above-mentioned diffracted light components from the isolated pattern.

In another embodiment (FIG. 5C), each of the three light-receiving elements in the x" direction shown in FIG. 5B is divided into three sections in the y" direction to constitute light-receiving elements having diffracted light discrimination performance in the y" direction, thereby increasing resolutions in both the x" and y" directions. A maximum angle BM or BN defined between adjacent light-receiving elements (28 and 31; 29 and 32; 30 and 33; 31 and 34; 32 and 35; 33 and 36; 28 and 29; 31 and 32; 34 and 35; 29 and 39; 32 and 33; 35 and 36) is set to be equal to or smaller than the pitch between adjacent diffracted light components in a corresponding one of the x" and y" directions. An angle $\beta x''$ or $\beta y''$ defined between light-receiving elements (28 and 34; 29 and 35; 30 and 36; 28 and 30; 31 and 33; 34 and 36) located at the two ends in each of the x" and y" directions is substantially equal to the angular aperture $\gamma$ of incident light I. FIG. 5D shows still another embodiment wherein light-receiving elements are arranged at a high density in a grid pattern. In this case, a maximum angle BM' or BN' defined between adjacent light-receiving elements (e.g., 43 and 50; 79 and 80) is set to be equal to or smaller than the pitch between adjacent diffracted light components in a corresponding one of the x" and y" directions. An angle $\beta x''$ or $\beta y''$ defined between light-receiving elements (e.g., 37 and 43) located at the two ends in each of the x" and y" directions is substantially equal to the angular aperture of incident light I. Note that the limit resolution in the x" direction is BM', and the limit resolution in the y" direction is BN'. When it is difficult to constitute light-receiving elements at a high density, the light-receiving surfaces may be constituted by a bundle of fibers, and received light components may be guided to the corresponding light-receiving elements via the fibers. In this manner, when the light-receiving elements are arranged as shown in FIGS. 5C and 5D, signals from the respective light-receiving elements (nine elements in FIG. 5C; 49 elements in FIG. 5D) are independently processed, and are input to the AND gate 109.

The circuit pattern P1 shown in FIG. 4A has two periodic directions having an equal angle $\theta_P$ in the X direction, the periodic direction of the distribution of diffracted light components on the normal projection view (FIG. 4B) depends on $\theta_P$, and the angle of the periodic direction is changed with respect to the X direction. However, diffracted light components always have periodicity in a direction parallel to or perpendicular to the X direction. Therefore, when the reference X and Y directions of the substrate 15 are taken into consideration, the aligning directions x" and y" of the light-receiving elements shown in FIGS. 5A to 5D can be aligned in the reference X and Y directions. For example, light-receiving elements (21a and 22a; 21b and 22b) may be arranged on the normal projection view, so that the longitudinal direction thereof is parallel to or perpendicular to the X direction, as shown in FIG. 4C. In other words, the light-receiving elements may be juxtaposed in a direction parallel to or perpendicular to the X direction.

Figure 6:
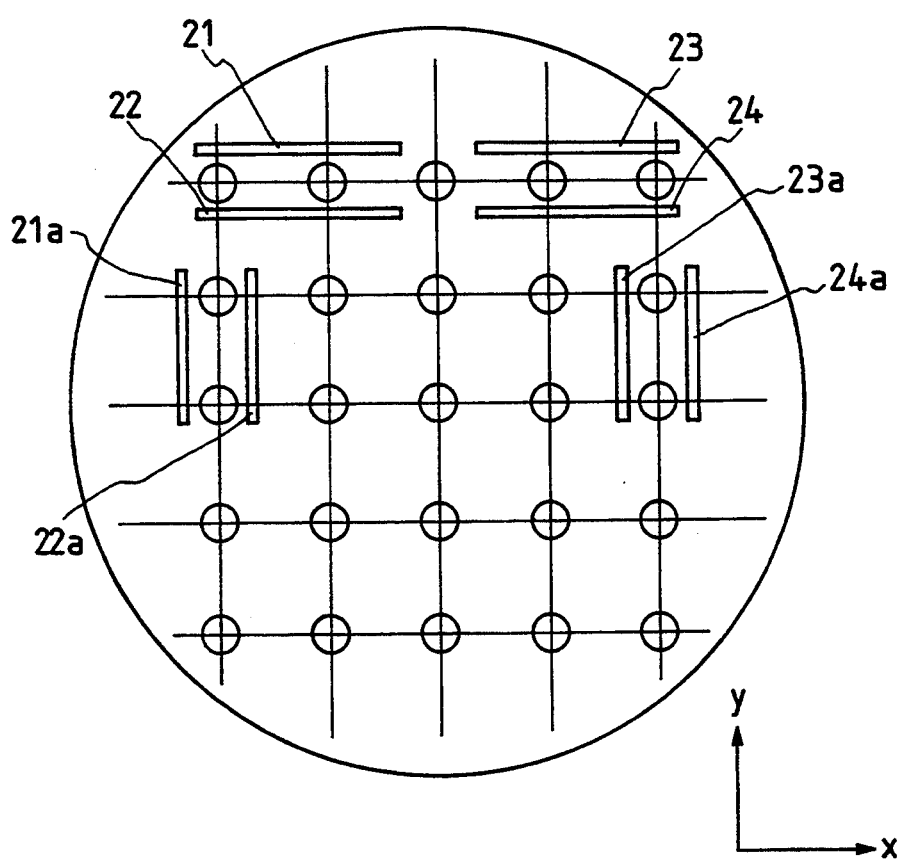
FIG. 6 is a normal projection view showing an arrangement suitable for a circuit pattern having two periodic directions in the X and Y directions.
Figure 12A:
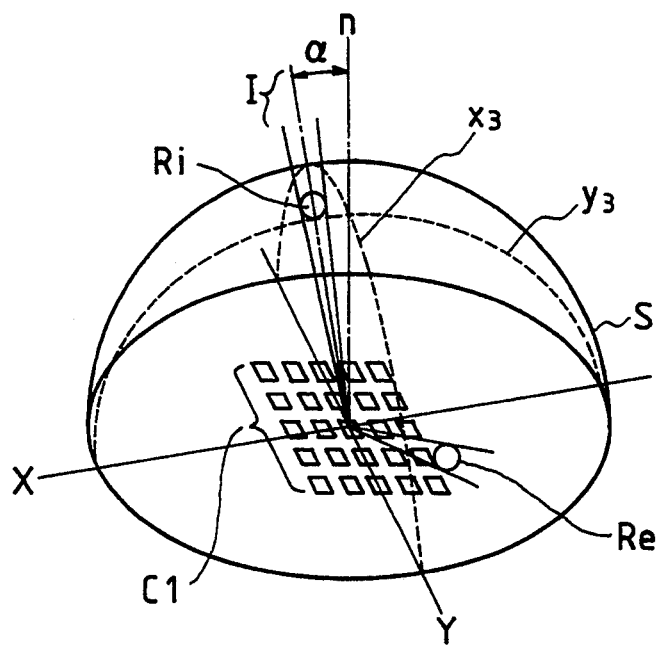
FIG. 12A shows a circuit pattern having two periodic directions in the X and Y directions.
Figure 12B:
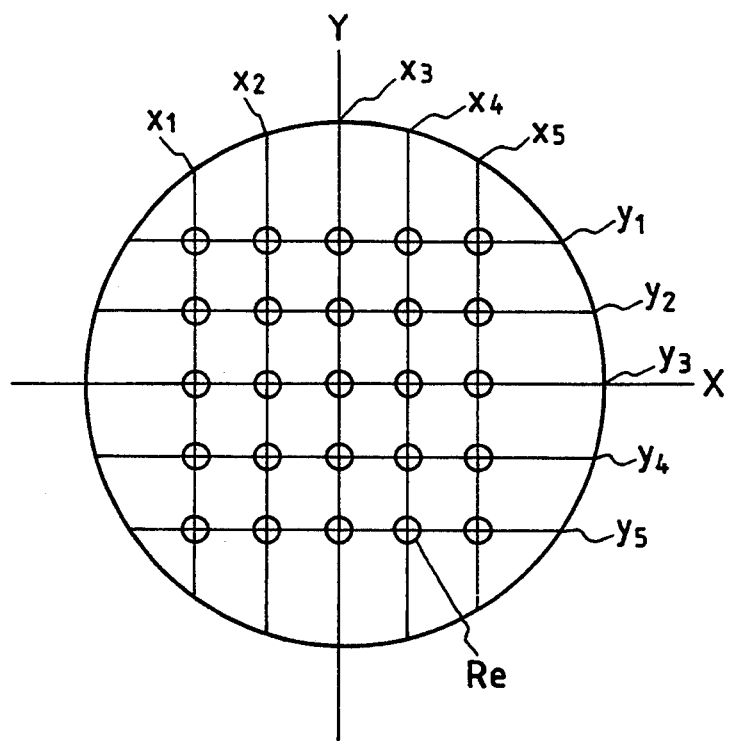
FIG. 12B is a normal projection view showing the distribution of diffracted light components from the pattern shown in FIG. 12A.
Figure 13A:
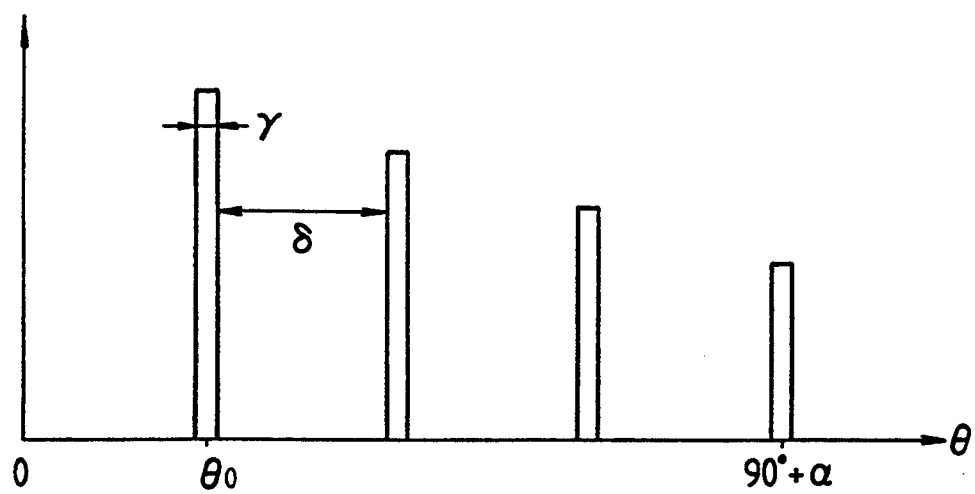
FIGS. 13A and 13B are graphs showing the strength of diffracted light.
Figure 13B:
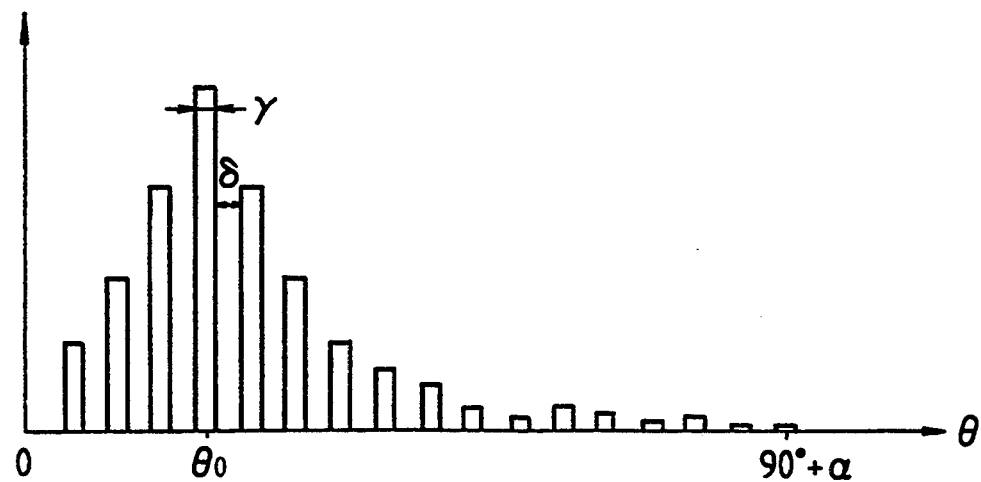
Figure 14A:
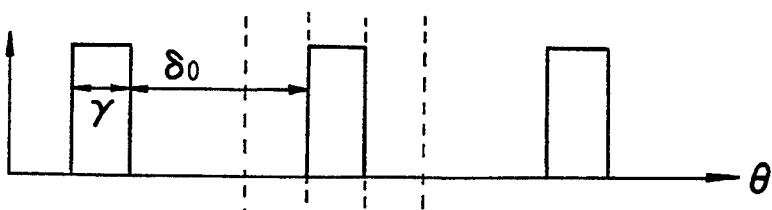
Figure 14B:
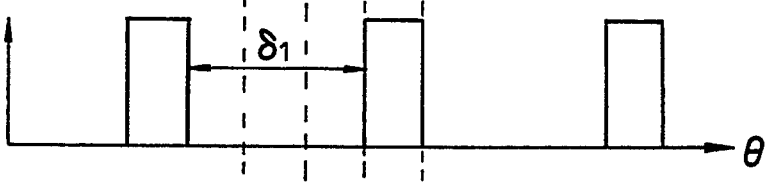
Figure 14C:
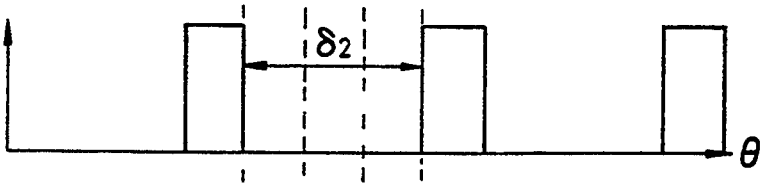
Figure 14D:
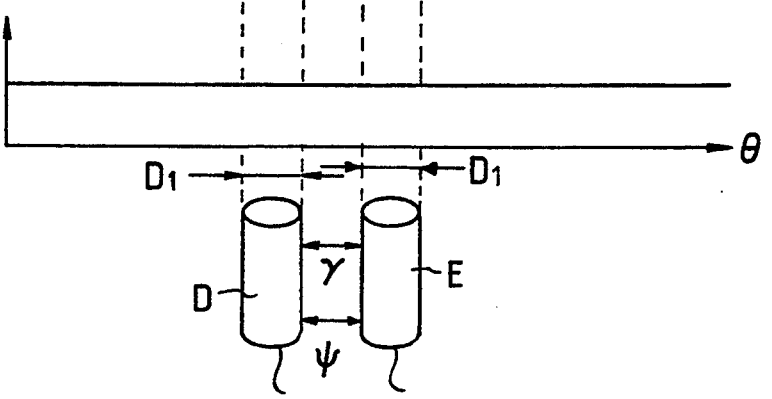
Figure 17:
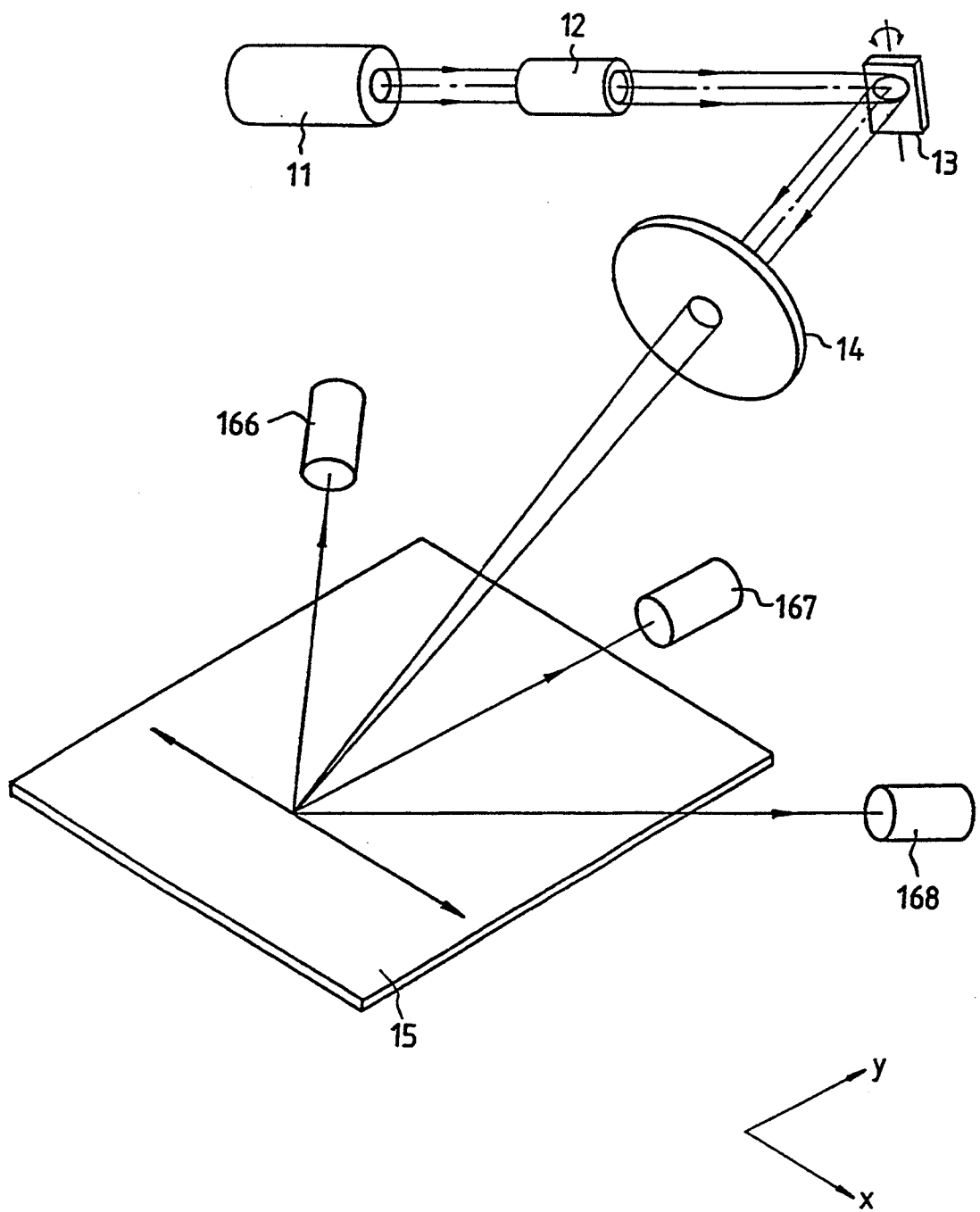
FIG. 17 is a perspective view showing an arrangement of a conventional foreign particle detecting apparatus.

As described above, the circuit pattern of a high-integration LSI often has periodicity in both the X and Y directions. A circuit pattern shown in FIGS. 12A and 12B has periodicity in both the X and Y directions. For example, light-receiving elements (21 and 22; 23 and 24; 21a and 22a; 23a and 24a) may be arranged on the normal projection view, so that the longitudinal direction thereof is parallel to or perpendicular to the X direction, as shown in FIG. 6. In other words, the light-receiving elements may be arranged to be juxtaposed in a direction parallel to or perpendicular to the X direction.

The third embodiment will be described below.

Figure 7A:
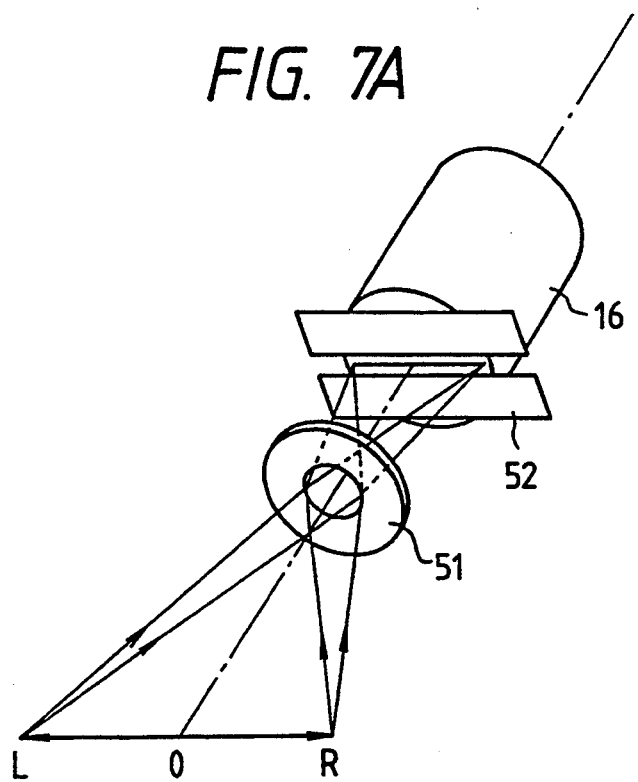
FIG. 7A is a perspective view showing the principle of the third embodiment of the present invention.
Figure 7B:
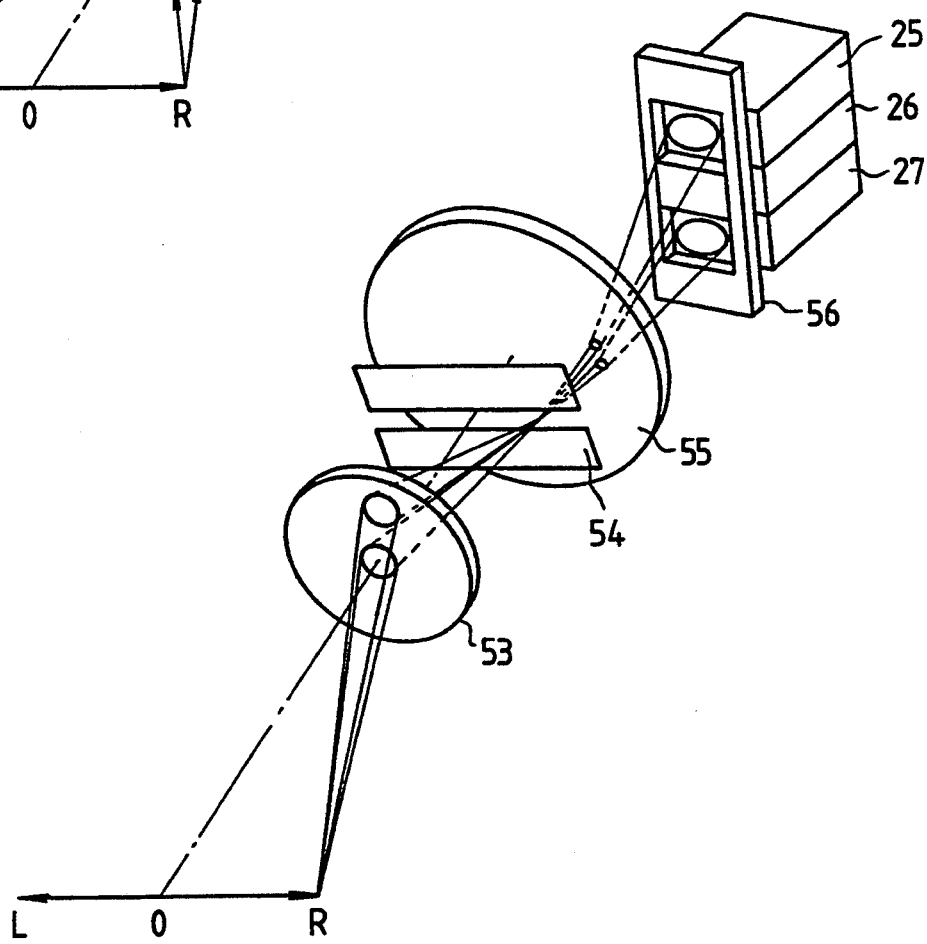
FIG. 7B is a perspective view showing an arrangement suitable for the third embodiment of the present invention.

In each of the above embodiments, diffracted light components are directly incident on the light-receiving elements. In this embodiment, however, diffracted light components are received via a lens system for shielding stray light produced from positions other than light scanning positions on the substrate 15. In the principle of this embodiment, stray light is removed using an image surface slit 52 arranged to be substantially parallel to a scanning line L-O-R at a position image-conjugate with the substrate 15 via a focusing lens 51, and light components are then received by a light-receiving element 16 arranged on an image surface, as shown in FIG. 7A. Since the detection means in each of the first and second embodiments of the present invention is constituted by a plurality of adjacent light-receiving elements, as shown in FIGS. 1 and 3, a single focusing lens is conveniently used by a plurality of light-receiving elements. FIG. 7B shows a detection means including a light-receiving optical system in this case. The detection means is arranged near an f-θ lens 14 like in the first and second embodiments. In FIG. 7B, stray light is removed from a light beam incident on a focusing lens 53, which is arranged in an optical path between diffracted light and light-receiving elements, by an image surface slit 54 arranged to be substantially parallel to the scanning line L-O-R at a position image-conjugate with the substrate 15, and the light beam is then incident on a field lens 55. The light beam is then incident on light-receiving elements 25 and 27 arranged near a pupil conjugate plane of the field lens 55. In this case, a variable aperture stop 56 is arranged in front of the light-receiving surfaces of the light-receiving elements 25, 26, and 27 so as to be able to select an angular width and angular interval of received light (an angular width and angular interval of the light-receiving surface), and the number of light-receiving elements. The arranging direction of light-receiving elements can be changed by a mechanism (not shown) for rotating the light-receiving elements themselves. For this reason, the angular width and angular interval of the light-receiving surface, the number of light-receiving elements, and the arranging direction of the light-receiving elements can be adjusted in accordance with foreign matter or a circuit pattern. Light-receiving elements may be arranged, as shown in FIG. 5D, and an aperture stop is arranged in front of these light-receiving elements so as to adjust, e.g., the angular width of received light, or to electrically adjust the angular width, angular interval, number, and arranging direction of the light-receiving elements.

FIG. 7B shows a case wherein the aperture stop in front of the light-receiving element 26 is closed, and two light-receiving elements are selected. The aperture stop and the rotation mechanism may be arranged in a case wherein light detection is performed without going through a lens system, i.e., in the first and second embodiments.

What is claimed is:

1. A foreign particle detecting apparatus which comprises:
   (a) a light source for radiating light onto a surface on which a miniaturized pattern is formed;
   (b) focusing means for focusing the light radiated by said light source onto said surface with a predetermined angular aperture;
   (c) moving means for moving the focused light relative to said surface;
   (d) detection means including an array of light-receiving elements for receiving light from said surface and independently outputting photoelectric signals according to the quantity of light received, focused light incident on said miniaturized pattern producing discrete diffracted light components having a periodic distribution in a first direction, n light-receiving elements of said array being arranged in order along a direction of arrangement determined by said first direction, the minimum spatial angle defined between light-receiving elements located at respective ends of said order being substantially equal to or slightly larger than said angular aperture of the focused light, and the maximum spatial angle defined between adjacent light-receiving elements in said order being equal to or smaller than the pitch between adjacent diffracted light components along said direction of arrangement; and
   (e) discrimination means for discriminating whether a foreign particle is present on said surface by whether the quantity of light received by each of said n light-receiving elements is equal to or greater than a predetermined threshold.

2. An apparatus according to claim 1, wherein n is 2.

3. An apparatus according to claim 1, wherein n is at least 3.

4. An apparatus according to claim 1, wherein said discrete diffracted light components have a periodic distribution in a second direction different from said first direction, m light-receiving elements of said array being arranged in a further order in a further direction of arrangement determined by said second direction, the minimum spatial angle defined between light-receiving elements located at respective ends of the further order being substantially equal to or slightly larger than said angular aperture of the focused light, and the maximum spatial angle defined between adjacent light-receiving elements in said further order being equal to or smaller than the pitch of adjacent diffracted light components along said further direction of arrangement;

said discrimination means discriminating whether a foreign particle is present on said surface by whether the quantity of light received by each of said n light receiving elements and each of said m light receiving elements is equal to or greater than a predetermined threshold.

5. An apparatus according to claim 4, wherein m is 2.

6. An apparatus according to claim 4, wherein m is at least 3.

7. An apparatus according to claim 1, wherein the light-receiving elements of said array form a grid pattern.

8. An apparatus according to claim 1, wherein the n light-receiving elements comprise at least three light-receiving elements having substantially the same angular aperture, the minimum spatial angle between the light-receiving elements at the respective ends of said order is substantially equal to the angular aperture of the focused light, and the remaining light-receiving elements of said order are arranged at equal intervals dividing the angular aperture of the focused light.

9. An apparatus according to claim 1, wherein each of said n light-receiving elements has a light-receiving surface with a length dimension and a smaller width dimension, and wherein the width dimension is along said direction of arrangement.

10. An apparatus according to claim 1, wherein said detection means has an optical system for directing light from said surface to said n light-receiving elements and wherein each of said n light-receiving elements has a light-receiving surface disposed at a position corresponding to a pupil plane of said optical system; and
said surfaces of n light-receiving elements are defined so as to conform to the spatial angle relation of said n light-receiving elements.

11. An apparatus according to claim 10, wherein said moving means moves the focused light relative to said surface along a scanning line, and
further comprising a slit,
said slit being disposed near a conjugate plane of said surface with respect to said optical system, for blocking stray light and for creating only light information from said scanning line.

12. An apparatus according to claim 10, wherein said detection means includes optical fibers for transmitting light from said surface to each of said n light-receiving elements,
input-ends of said optical fibers being disposed at said pupil plane of said optical system.

13. An apparatus according to claim 1, wherein said detection means includes optical fibers for transmitting light from said surface to each of said n light-receiving elements.

14. An apparatus according to claim 1, wherein each of said n light-receiving elements has a light-receiving surface, and further comprising means for deciding at least one of an angular width of the light-receiving surface, an angular interval between light-receiving surfaces, a direction of arrangement of the light-receiving surfaces, and the number of light-receiving surfaces.

15. An apparatus according to claim 14, wherein said deciding means comprises a variable slit.

16. An apparatus according to claim 14, wherein said deciding means electrically selects the light-receiving elements.

17. An apparatus according to claim 1, wherein said moving means moves the focused light relative to said surface along a scanning line, and further comprising means defining a slit adjacent to each of said n light-receiving elements and substantially parallel to said scanning line for shielding each of said light-receiving elements from stray light.

18. An apparatus according to claim 1, wherein said surface is on an equatorial plane of an imaginary sphere having at its center the origin of a two dimensional orthogonal coordinate system on said plane, said moving means moves said focused light along a scanning line coincident with one coordinate axis of said system and having said origin as its center, a principal ray of said focused light incident on said origin lies in a plane perpendicular to said equatorial plane and perpendicular to said scanning line, said miniaturized pattern has a periodic direction, and said direction of arrangement of said n light-receiving elements is defined by a line of intersection with the surface of said sphere of a plane perpendicular to said equatorial plane and parallel to said periodic direction.

19. An apparatus according to claim 1, wherein said surface is on an equatorial plane of an imaginary sphere having at its center the origin of a two dimensional orthogonal coordinate system on said plane, said moving means moves said focused light along a scanning line coincident with one coordinate axis of said system and having said origin as its center, a principal ray of said focused light incident on said origin lies in a plane perpendicular to said equatorial plane and perpendicular to said scanning line,
said miniaturized pattern has two periodic directions and has symmetric pattern disposition with respect to a predetermined reference direction on said surface, and
said direction of arrangement of said n light-receiving elements is defined by a line of intersection with the surface of said sphere of a plane perpendicular to said equatorial plane and parallel to said reference direction or perpendicular to said reference direction.

20. A foreign particle detecting apparatus which comprises:
(a) a light source for radiating light onto a surface on which a miniaturized pattern is formed;
(b) focusing means for focusing the light radiated by said light source onto said surface with a predetermined angular aperture;
(c) moving means for moving the focused light relative to said surface:
(d) at least two detection means disposed so as to look to an incidence position of said light on said surface from different viewing directions, each of said at least two detection means including an array of light-receiving elements for receiving light from said surface and independently outputting photoelectric signals according to the quantity of light received, focused light incident on said miniaturized pattern producing discrete diffracted light components having a periodic distribution in a first direction, n light-receiving elements of each array being arranged in order along a direction of arrangement determined by said first direction, the minimum spatial angle defined between light-receiving elements located at respective ends of said order being substantially equal to or slightly larger than said angular aperture of the focused light, and the maximum spatial angle defined between adjacent light-receiving elements in said order being equal to or smaller than the pitch between adjacent diffracted light components along said direction of arrangement; and
(e) discrimination means for discriminating whether a foreign particle is present on said surface by whether the quantity of light received by each of said n light-receiving elements in each of said at least two detection means is equal to or greater than a predetermined threshold.

21. A foreign particle detecting apparatus which comprises:
(a) a light source for radiating light onto a surface on which a miniaturized pattern is formed;
(b) focusing means for focusing the light radiated by said light source onto said surface with a predetermined angular aperture;
(c) moving means for moving the focused light relative to said surface;
(d) detection means including an array of light-receiving elements for receiving light from said surface and independently outputting photoelectric signals according to the quantity of light received, focused light incident on said miniaturized pattern producing discrete diffracted light components having a periodic distribution in a first direction, n light-receiving elements of said array being arranged in order along a direction of arrangement determined by said first direction,
the minimum spatial angle defined between light-receiving elements located at respective ends of said order being substantially equal to or slightly larger than a spatial angle of any one diffracted light component directed toward said detection means from said surface,
and the maximum spatial angle defined between adjacent light-receiving elements in said order being equal to or smaller than the pitch between adjacent diffracted light components along said direction of arrangement; and
(e) discrimination means for discriminating whether a foreign particle is present on said surface by whether the quantity of light received by each of said n light-receiving elements is equal to or greater than a predetermined threshold.

22. An apparatus according to claim 21, wherein the n light-receiving elements comprise at least three light receiving elements having substantially the same angular aperture, the minimum spatial angle between the light-receiving elements at the respective ends of said order is substantially equal to said spatial angle of said one diffracted light component, and the remaining light-receiving elements of said order are arranged at equal intervals dividing said spatial angle of said one diffracted light component.

23. An apparatus according to claim 21, wherein said detection means has an optical system for directing light from said surface to said n light-receiving elements and wherein each of said n light-receiving elements has a light-receiving surface disposed at a position corresponding to a pupil plane of said optical system, and
said surfaces of n light-receiving elements are defined so as to conform to the spatial angle relation of said n light-receiving elements.

24. An apparatus according to claim 21, wherein said surface is on an equatorial plane of an imaginary sphere having at its center the origin of a two dimensional orthogonal coordinate system on said plane, said moving means moves said focused light along a scanning line coincident with one coordinate axis of said system and having said origin as its center, a principal ray of said focused light incident on said origin lies in a plane perpendicular to said equatorial plane and perpendicular to said scanning line,
said miniaturized pattern has a periodic direction, and said direction of arrangement of said n light-receiving elements is defined by a line of intersection with the surface of said sphere of a plane perpendicular to said equatorial plane and parallel to said periodic direction.

25. An apparatus according to claim 21, wherein said surface is on an equatorial plane of an imaginary sphere having at its center the origin of a two dimensional orthogonal coordinate system on said plane, said moving means moves said focused light along a scanning line coincident with one coordinate axis of said system and having said origin as its center, a principal ray of said focused light incident on said origin lies in a plane perpendicular to said equatorial plane and perpendicular to said scanning line,
said miniaturized pattern has two periodic directions and has symmetric pattern disposition with a predetermined reference direction on said surface, and
said direction of arrangement of said n light-receiving elements is defined by a line of intersection with the surface of said sphere of a plane perpendicular to said equatorial plane and parallel to said reference direction or perpendicular to said reference direction.

26. A foreign particle detecting apparatus which comprises:
(a) a light source for radiating light onto a surface on which a miniaturized periodic pattern having two periodic directions is formed;
(b) focusing means for focusing the light radiated by said light source onto said surface with a predetermined angular aperture:
(c) moving means for moving the focused light relative to said surface;
(d) at least two detection means disposed so as to look to an incidence position of said focused light on said surface from different viewing directions, each of said at least two detection means including an array of light-receiving elements for receiving light from said surface and independently outputting photoelectric signals according to the quantity of light received, focused light incident on said miniaturized periodic pattern producing discrete diffracted light components having a periodic distribution in a first direction, n light-receiving elements of each array being arranged in order along a direction of arrangement determined by said first direction,
the minimum spatial angle defined between light-receiving elements located at respective ends of said order being substantially equal to or slightly larger than a spatial angle of any one diffracted light component directed toward said detection means from said surface,
and the maximum spatial angle defined between adjacent light-receiving elements in said order being equal to or smaller than the pitch between adjacent diffracted light components along said direction of arrangement; and
(e) discrimination means for discriminating whether a foreign particle is present on said surface by whether the quantity of light received by each of said n light-receiving elements in each said at least two detection means is equal to or greater than a predetermined threshold.

* * * * *